(12) United States Patent
Cheng et al.

US011234762B2

(10) Patent No.: US 11,234,762 B2
(45) Date of Patent: Feb. 1, 2022

(54) METHOD AND DEPLOYABLE MULTI-SPINE APPARATUS FOR CATHETER-BASED RENAL DENERVATION

(71) Applicants: AGENCY FOR SCIENCE, TECHNOLOGY AND RESEARCH, Singapore (SG); Handok Kalos Medical, Seoul (KR)

(72) Inventors: Ming-Yuan Cheng, Singapore (SG); Songsong Zhang, Singapore (SG); Alex Yuandong Gu, Singapore (SG); Andrew Benson Randles, Singapore (SG); Ee Lim Tan, Singapore (SG); Pushpapraj Singh, Singapore (SG); Kwan Ling Tan, Singapore (SG); Weiguo Chen, Singapore (SG); Ruiqi Lim, Singapore (SG); Ramona Damalerio, Singapore (SG); Surasit Chungpaiboonpatana, Singapore (SG); Eul Joon Park, Seoul (KR); Jung Soo Oh, Seoul (KR); Jae Hyung Park, Seoul (KR); In Hee Bae, Seoul (KR)

(73) Assignees: AGENCY FOR SCIENCE, TECHNOLOGY AND RESEARCH, Singapore (SG); HANDOK KALOS MEDICAL, Seoul (KR)

( * ) Notice: Subject to any disclaimer, the term of this patent is extended or adjusted under 35 U.S.C. 154(b) by 695 days.

(21) Appl. No.: 16/063,242

(22) PCT Filed: Dec. 15, 2016

(86) PCT No.: PCT/SG2016/050606
§ 371 (c)(1),
(2) Date: Jun. 15, 2018

(87) PCT Pub. No.: WO2017/105351
PCT Pub. Date: Jun. 22, 2017

(65) Prior Publication Data
US 2018/0368914 A1 Dec. 27, 2018

(30) Foreign Application Priority Data

Dec. 15, 2015 (SG) .......................... 10201510264Y

(51) Int. Cl.
*A61B 18/14* (2006.01)
*A61L 29/08* (2006.01)
(Continued)

(52) U.S. Cl.
CPC .......... *A61B 18/1492* (2013.01); *A61L 29/08* (2013.01); *A61M 25/0009* (2013.01);
(Continued)

(58) Field of Classification Search
CPC ..... A61B 18/1492; A61B 18/18; A61B 18/14; A61B 18/02; A61B 18/082; A61B 18/00; A61N 1/36117; A61N 1/05; A61F 2/07
See application file for complete search history.

(56) References Cited

U.S. PATENT DOCUMENTS 8,728,137 B2   5/2014  Zarins et al.
8,979,839 B2 * 3/2015  De La Rama ..... A61B 18/1492
                                              606/41
(Continued)

FOREIGN PATENT DOCUMENTS

KR      20140100168 A    8/2014
WO   WO 2009/085108 A1   7/2009
(Continued)

OTHER PUBLICATIONS

Brace; et al, Radiofrequency and Microwave Ablation of Liver, Hung, Kidney and Bone: What are the Differences, Curr. Probl. Diagn. Radiol. 38. 135-143. 2009. 17 pp.
(Continued)

*Primary Examiner* — Manuel A Mendez
(74) *Attorney, Agent, or Firm* — Womble Bond Dickinson (US) LLP

(57) ABSTRACT

A device for vascular denervation comprising a catheter for insertion into a vessel, at least one elongated catheter arm
(Continued)

having alternating regions of flexible joints and rigid blocks along the at least one catheter arm, wherein each of the at least one catheter arm comprises at least one tactile sensor and at least one temperature sensor; at least one electrode and electrical circuitry disposed on each of the at least one catheter arm and at least one linkage connected to all of the elongated catheter arms. A method for batch fabricating a plurality of catheter arms for the vascular denervation device is also provided and comprises the steps of depositing a first polymer coating on a semiconductor substrate, forming metal traces on the first polymer coating, patterning and etching the substrate to the first polymer coating to create flexible joint regions.

17 Claims, 19 Drawing Sheets

(51) Int. Cl.
*A61M 25/00* (2006.01)
*A61B 18/00* (2006.01)
*A61B 90/00* (2016.01)

(52) U.S. Cl.
CPC .............. *A61M 25/0045* (2013.01); *A61B 2018/00136* (2013.01); *A61B 2018/00148* (2013.01); *A61B 2018/00267* (2013.01); *A61B 2018/00434* (2013.01); *A61B 2018/00511* (2013.01); *A61B 2018/00577* (2013.01); *A61B 2018/00791* (2013.01); *A61B 2018/00875* (2013.01); *A61B 2090/065* (2016.02); *A61L 2420/02* (2013.01)

(56) References Cited

U.S. PATENT DOCUMENTS

| | | | |
|---|---|---|---|
| 10,111,705 | B2* | 10/2018 | Watson .................... A61B 1/05 |
| 2012/0296329 | A1 | 11/2012 | Kok-Hwee |
| 2014/0018888 | A1 | 1/2014 | Ostroot et al. |
| 2014/0107639 | A1 | 4/2014 | Zhang et al. |
| 2014/0200578 | A1 | 7/2014 | Groff et al. |
| 2016/0073960 | A1* | 3/2016 | Jung .................... A61B 5/6858 600/374 |

FOREIGN PATENT DOCUMENTS

| | | |
|---|---|---|
| WO | WO 2010/078175 A1 | 7/2010 |
| WO | WO 2011/060339 A1 | 5/2011 |
| WO | WO 2013/163322 A1 | 10/2013 |
| WO | WO 2014/158708 A1 | 10/2014 |

OTHER PUBLICATIONS

DiBona; "GF. Neural Control of the Kidney Past Present, and Future". Hypertension, 41, 621-624, 2003. 4 pp.

Douma; et al.; "Renal Sympathetic Denervation: The Jury is Still Out"; The Lancet; 2010; 3 pp.
Kearney; et al.; "Global Burden of Hypertension: Analysis of Worldwide Data"; The Lancet; vol. 365; 2005. 7 pp.
Klinker, Lauren; et al., "Balloon Catheters with Integrated Stretchable Electronics for Electrical Stimulation, Ablation and Blood Flow Monitoring"; Extreme Mechanics Letters vol. 3, Jun. 2015, pp. 45-54; 10 pp.
Myat; et al., Renal Sympathetic Denervation Therapy for Resistant Hypertension: A contemporary Synopsis and Future Implications, Circ. Cardiovasc Interv. 6, 184-197, 2013. 14 pp.
Mabin; et al.; "First Experience with Endovascular Ultrasound Renal Denervation for the Treatment of Resistant Hypertation"; EuroIntervention; 8:57-61; (2012). 5 pp.
Morrisey; et al.; "Sympathectomy in the Treatment of Hypertension Review of 122 Cases"; The Lancet, Original Articles; Feb. 28, 1953. 6 pp.
Sapoval; et al.; "Endovascular Renal Artery Denervation: Why, When, and How?"; Cardiovasc Intervent Radiol; 35:463-471; (2012); 9 pp.
Schlaich; et al. "Renal Denervation and Hypertension"; American Journal of Hypertension, vol. 24, No. 6; 2011. 8 pp.
St. Jude Medical; "Receives European Approval for Ne Renal Denervation System that Reduces Total Ablation Time by More Than 80 Percent" St. Jude Medical News released Aug. 29, 2013; 4 pp. http://media.sim.com/newsroom/news-releases-details/2013/St-Jude-Medical-Receives-European-Approval-for-New-Renal-Denervation-System-that-Reduces-Total-Ablation-Time-by-More-80-Percent08292013/default.aspx.
St.Jude.Medical; EngligHTN 1: 24-Month Clinical Data, EnlightHTN, Multi-electrode Renal Denervation System, St. Jud Medical Inc. 6 pp. http://geoselector.sjm.com/ConfirmationPage?url=http%3a%2fprofessional-intl.sim.com%3a880%2fproducts%2fvas%frenal-denervation%2frenal-denervation-system%2fenlightn-multi-electrode-renal-denervation-system&regionsId={3277730C-7265-4D8B-B650-FD9CF89A0FC2}language=en-INT.
Vasan; "Assessment of frequency of progression to hypertension in non-hypertensive participants in the Framingham Heart Study: a cohort study". Lancet 2001; 358: 1682-86. 6 pp.
World Health Organization; "The top 10 cause of death"; 2018. 8 pp. Available at: http://www.who.int/mediacentre/factssheets/fs310/en/index.html.
IP Office of Singapore—Notification of Transmittal of the International Search Report & the Written Opinion of the International Searching Authority, or the Declaration, with the ISR & Written Opinion dated Mar. 2, 2017 for Int'l. Application No. PCT/SG2016/050606 (14 pgs).
IP Office of Singapore—Int'l. Preliminary Report on Patentability dated Jun. 3, 2018 with Chapter II Demand with Article 34 Amendment dated Oct. 13, 2017 for International Application No. PCT/SG2016/050606 (30 pgs).
Tan, et al., "Evaluation of Biodegradable Coating on the Stiffness Control of the Polyimide-based Probe used in Neural Devices." *Electronics Packaging and Technology Conference (EPTC), 2015 IEEE 17th*, Dec. 2, 2015, p. 7412287:1-4.

* cited by examiner

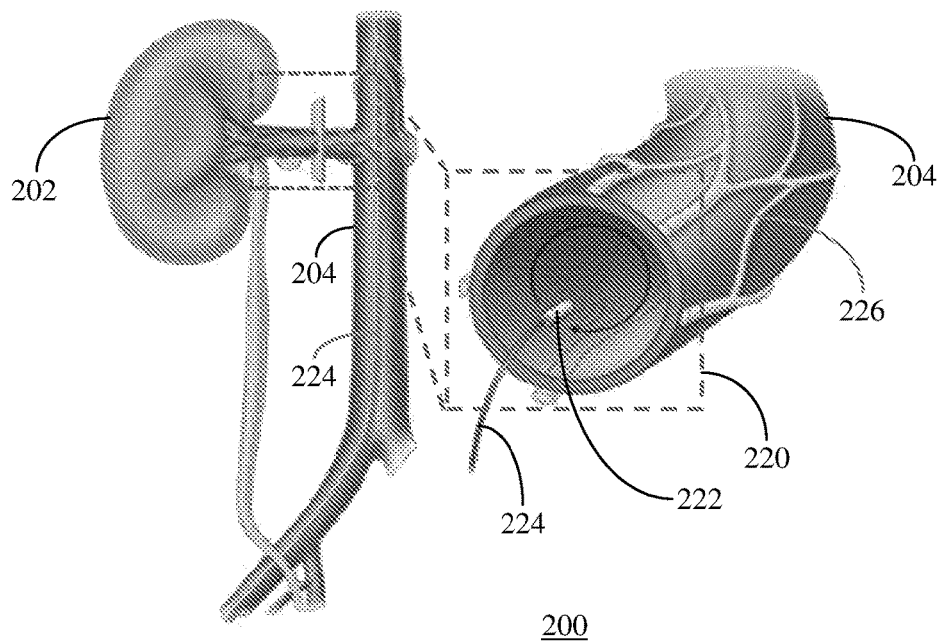
*FIG. 2A*
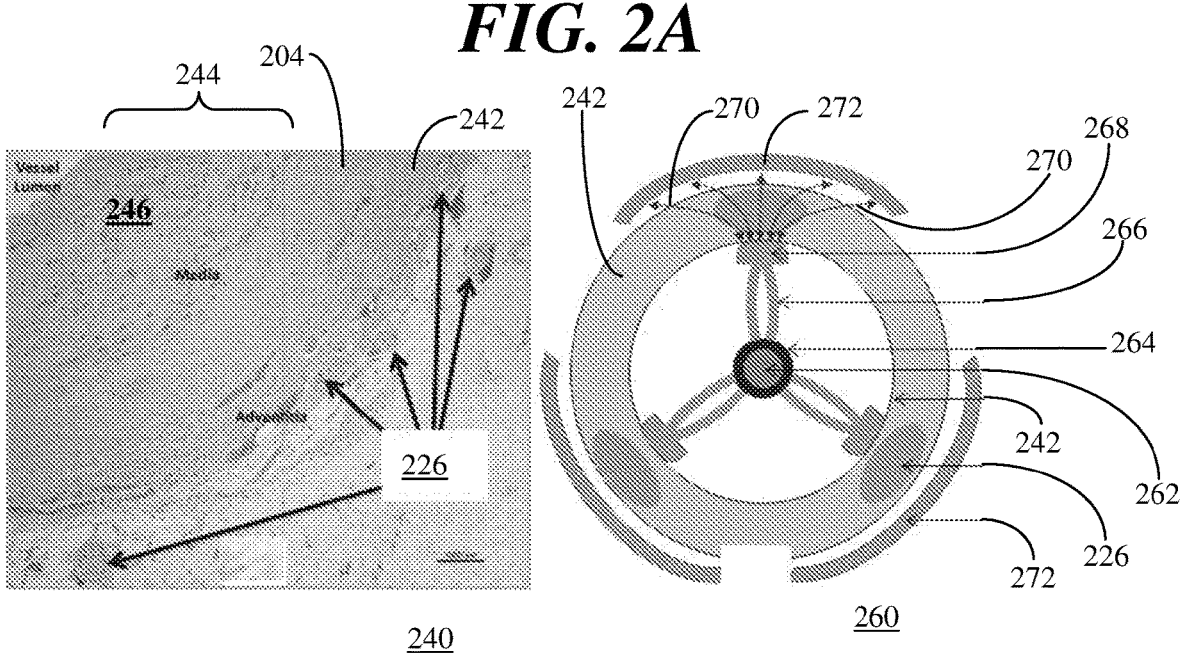
*FIG. 2B*   *FIG. 2C*

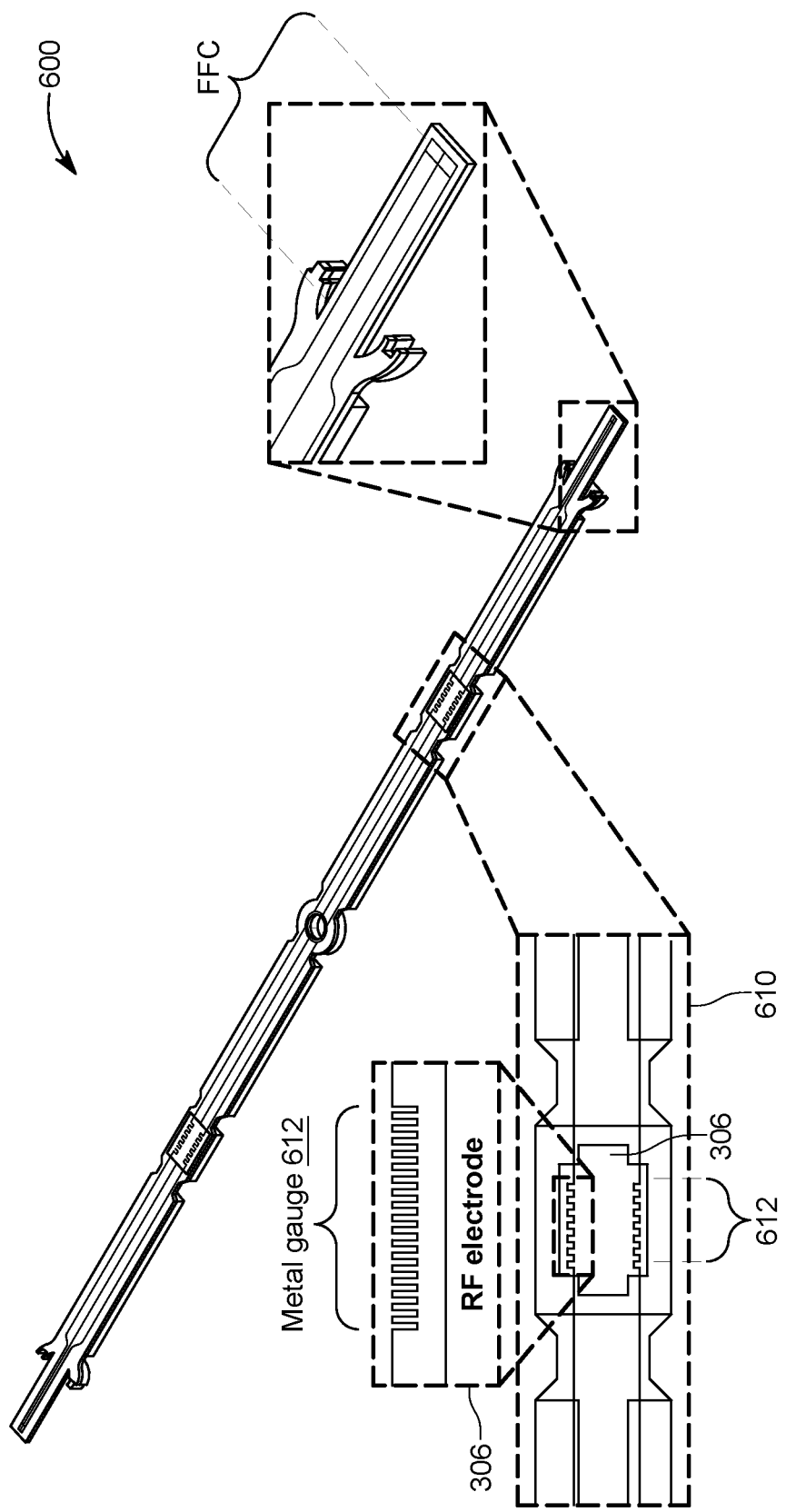

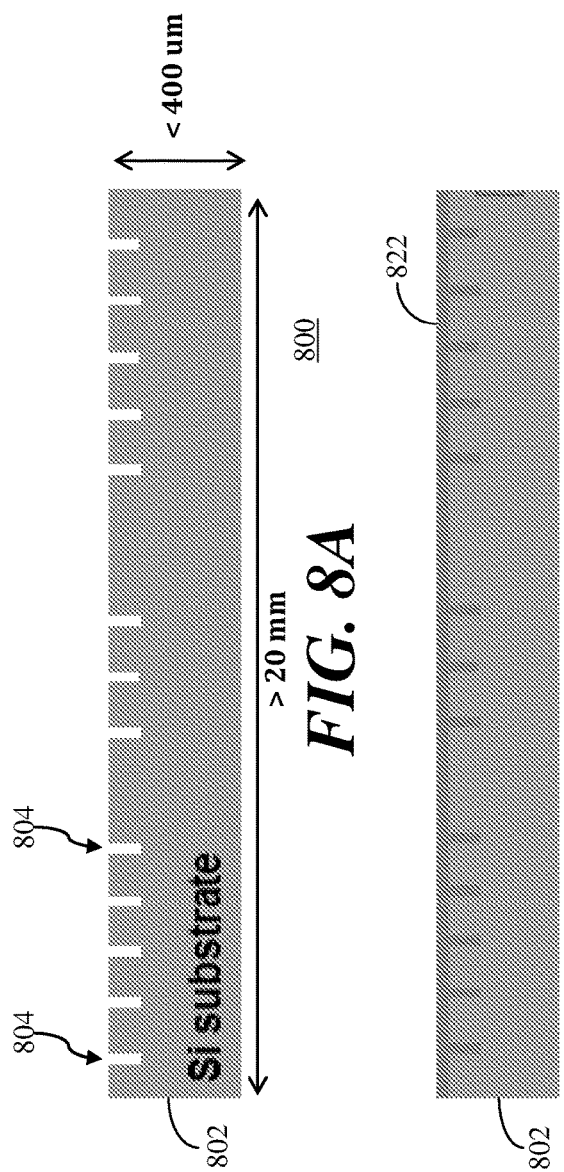
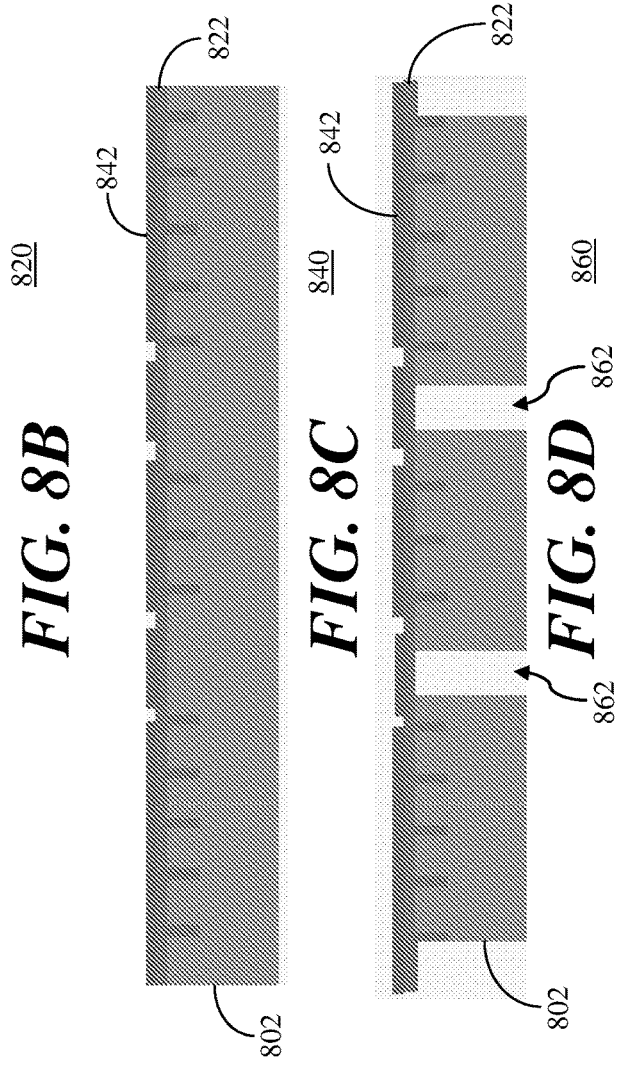
FIG. 8A
FIG. 8B
FIG. 8C
FIG. 8D

METHOD AND DEPLOYABLE MULTI-SPINE APPARATUS FOR CATHETER-BASED RENAL DENERVATION

CROSS-REFERENCE TO RELATED APPLICATIONS

This patent application is a U.S. National Phase application under 35 U.S.C. § 371 of International Application No. PCT/SG2016/050606, filed 15 Dec. 2016, entitled METHOD AND DEPLOYABLE MULTI-SPINE APPARATUS FOR CATHETER-BASED RENAL DENERVATION, which claims priority from Singapore Patent Application No. 10201510264Y filed on 15 Dec. 2015.

TECHNICAL FIELD

The present invention generally relates to methods and apparatuses for renal denervation, and more particularly relates to deployable multi-spine catheter-based renal denervation devices and methods for their fabrication.

BACKGROUND OF THE DISCLOSURE

Hypertension and its related conditions, heart failure and chronic kidney disease, represent a significant and growing global health issue. Hypertension is a common medical condition and the condition refers to high blood pressure (BP) in patients. Although an asymptomatic condition, when left untreated, chronic hypertension can significantly increase the risk of stroke, heart failure, chronic kidney disease and heart attack, posing serious health risks to those suffering from the disease. The prevalence of high blood pressure increases with age, obesity and sedentary lifestyles. Since all three factors are on the rise worldwide, hypertension treatment represents a large and growing clinical concern. This condition is a condition where the force that blood is exerting on the walls of the arteries of the body is higher than desirable and has a direct relation to increased risk of cardiovascular diseases.

Treatments for patients with hypertension consist of dietary restrictions/control, medicine or a combination of both. However, when more than three types of drug regimes have been used and blood pressure remains high, the condition is known as resistant hypertension. Resistant hypertension is uncontrolled BP despite the use of drugs from three or more antihypertensive classes at maximally tolerated doses and has become the focus of intense medical interest. About one in fifty patients with a new diagnosis of hypertension will develop resistant hypertension. In the 1950s, surgical renal denervation was shown to be a highly effective treatment for resistant hypertension, but the procedure was abandoned because of intolerable side effects such as bladder dysfunction and orthostatic. More recently, carotid baroreceptor surgery for resistant hypertension was investigated and results were encouraging, but this currently remains a surgical procedure. Now, catheter-based renal denervation has emerged as a potential minimally invasive strategy to treat resistant hypertension.

Currently, there are few technologies available. Most conventional technologies utilize balloon-based catheters or basket-design catheters with electrodes or temperature sensors being placed at defined positions (e.g. along a basket shaft, a catheter shaft or a surface of balloon) for renal denervation. Balloon catheterization is a typical technique where a balloon can be expanded within blood vessels according to the dimension of the vessels, which is convenient as the dimension of vessels differ for each individual patient and this can make sure that the electrodes are in contact with the vessel walls. However, a disadvantage of balloon catheters is that the blood flow may be blocked during inflation of the balloon. This issue can be solved by using a basket-design catheter where the electrodes are placed along the basket shaft and the deployment is achieved by a pulling-pushing mechanism of a movable component. Although the blood flow is not restricted as in the balloon-based catheter, there may be an issue regarding contact between the electrodes and the vessel walls. This contact issue could be due to the lack of a tactile sensor to assist in achieving effective contact between the electrodes and the vessel walls. The assembly works involved in these designs are manual and intensive, which has the added disadvantages of being not efficient and prone to errors.

Thus, what is needed are designs for renal denervation catheters which at least partially overcomes the drawbacks of present approaches. Furthermore, other desirable features and characteristics will become apparent from the subsequent detailed description and the appended claims, taken in conjunction with the accompanying drawings and this background of the disclosure.

SUMMARY

According to at least one embodiment of the present invention, a method for batch fabricating a plurality of catheter arms for vascular denervation is provided. The method includes depositing a first polymer coating on a semiconductor substrate and forming metal traces on the first polymer coating. The method further includes patterning and etching the substrate to the first polymer coating to create flexible joint regions and fabricating the plurality of catheter arms with flexible joint regions.

According to another embodiment of the present invention, a device for vascular denervation is provided. The device for vascular denervation includes a catheter for insertion into a vessel, at least one elongated catheter arm having alternating regions of flexible joints and rigid blocks and at least one linkage connected to all of the at least one elongated catheter arm. Two or more sensors, at least one electrode and electrical circuitry are disposed on each of the at least one catheter arm. The two or more sensors include at least one tactile sensor and at least one temperature sensor. The at least one electrode is for nerve ablation and the electrical circuitry disposed on each of the at least one catheter arm is coupled to inputs and outputs of the at least one electrode and the at least one sensor. The at least one linkage is connected to all of the at least one elongated catheter arm at substantially an end of the at least one elongated catheter arm for wrapping all of the at least one catheter arm around the catheter.

According to a further embodiment of the present invention a method for vascular denervation is provided. The method includes inserting a device including a catheter into a vessel and deploying at least one catheter arm of the device until it makes contact against a wall of the vessel, all of the at least one catheter arm disposed around the catheter. The method further includes monitoring an amount of contact of the at least one catheter arm with the wall of the vessel to determine that the amount of contact does not restrict fluid flow in the vessel and the amount of contact is sufficient for the vascular denervation by using at least one tactile sensor disposed on one of the at least one catheter arm. Finally, the method includes ablating targeted nerves by energizing at least one electrode disposed on one of the at least one catheter arm when in contact with the blood wall of the vessel. The tactile sensor determines that the amount of contact is sufficient for the vascular denervation in response to impedance detected by an impedance change element of the tactile sensor.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 2, comprising FIGS. 2A, 2B and 2C, depicts illustrations of conventional renal denervation, wherein FIG. 2A depicts a planar view of a kidney and its corresponding renal artery and a perspective cutaway view of the renal artery with a denervation catheter inserted therein, FIG. 2B depicts a histological section of a renal artery, and FIG. 2C depicts a side planar depiction of electrode deployment in a renal artery for renal denervation using a conventional basket shaped renal denervation system.

FIG. 3, comprising FIGS. 3A and 3B, depicts perspective views of a fabricated spine structure for a renal denervation system in accordance with a present embodiment, wherein FIG. 3A depicts a front top right perspective view of the spine structure and FIG. 3B depicts a front bottom left perspective view of the spine structure.

FIG. 5, comprising FIGS. 5A, 5B and 5C, depicts front top right perspective views illustrating operational deployment of the spine structure of FIG. 4 wrapped around a catheter in accordance with the present embodiment, wherein FIG. 5A depicts the undeployed spine structure on the catheter, FIG. 5B depicts the spine structure semi-deployed around the catheter, and FIG. 5C depicts the spine structure fully deployed around the catheter.

FIG. 6, comprising FIGS. 6A, 6B and 6C, depicts perspective views of the fabricated spine structure in accordance with the present embodiment, wherein FIG. 6A depicts a front top left perspective view of a two-spine structure highlighting various structural portions in insets, FIG. 6B depicts a front bottom right perspective view of the two-spine structure of FIG. 6A highlighting further structural features in an inset, and FIG. 6C depicts a front top left perspective view of a three-spine structure highlighting various structural portions in an inset.

FIG. 7, comprising FIGS. 7A and 7B, depicts perspective views of the catheter and spine structure in accordance with the present embodiment, wherein FIG. 7A depicts a front top right perspective view of the two-spine structure as it is assembled around the catheter and FIG. 7B depicts a front top right perspective view of the two-spine structure around the catheter and fully deployed showing a magnified view of the vessel wall contact portion of the spine in an inset.

FIG. 8, comprising FIGS. 8A, 8B, 8C and 8D, depicts side planar cutaway views of fabrication steps of the spine structure with integrated sensor and electrode devices in accordance with the present embodiment.

FIG. 9, comprising

FIG. 10, comprising FIGS. 10A, 10B and 10C, depict simulation-measured displacement forces on the spine structure in accordance with the present embodiment, wherein FIG. 10A depicts simulation-measured displacement forces on the spine structure with no silicon stiffener behind the spine structure's denervation electrode, FIG. 10B depicts simulation-measured displacement forces on the spine structure with a one millimeter (mm) thick silicon stiffener behind the spine structure's denervation electrode, and FIG. 10C depicts simulation-measured displacement forces on the spine structure with a 1.4 mm thick silicon stiffener behind the spine structure's denervation electrode.

And FIG. 11, comprising FIGS. 11A and 11B, depicts strain diagrams of bending modes of the spine structure in accordance with the present embodiment, wherein FIG. 11A depicts a strain diagram of a fully deployed spine structure in a first bending mode and FIG. 11B depicts a strain diagram of a partially deployed spine structure in a second bending mode.

Figure 1:
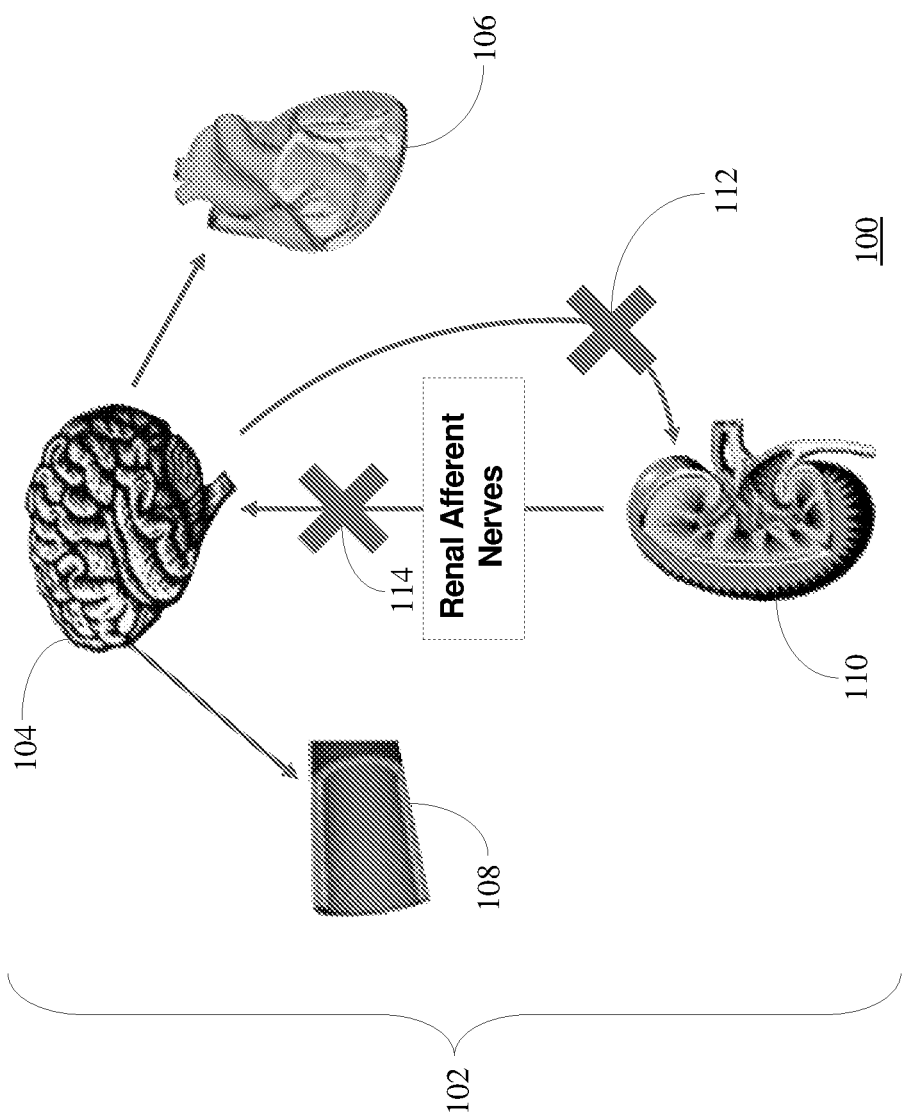
FIG. 1 depicts an illustration of a human sympathetic nerve system.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present a rollup, deployable multi-spine structure with integrated tactile/force sensors which can be applied for renal denervation on patients with resistant hypertension. Catheterization techniques are used to deliver the spine structure to targeted renal vessels. The structure is then deployed to allow electrodes integrated on the spine structure to carry out renal nerve ablation. Integrated sensors on the spine structure include temperature sensors, tactile sensors and radio frequency (RF) electrodes or heaters to enable effective contact between the electrodes and the renal vessel walls for enhanced, robust renal denervation. While the discussion in this detailed description describes methods, devices and systems for renal denervation, the methods, devices and systems are equally applicable to other vascular denervation systems.

The structure can be fabricated on a silicon wafer with current micromachining processes providing a highly scalable, high throughput product fabrication with simplified spine integration procedures, thereby lowering overall cost. In addition, the integrated tactile/force sensors provide a continuous monitoring of the contact condition between the renal vessel wall and the active electrode to facilitate surgical procedures and improve the efficiency of the nerve ablation during renal denervation.

Blood pressure (BP) measurement is now routine at most medical office visits. With the availability of inexpensive, reliable and easy-to-use portable digital blood pressure meters, many people also monitor their own BP at home. Nevertheless, hypertension is usually asymptomatic and remains under-diagnosed, particularly among people not receiving regular preventative medical examinations. Normal blood pressure is presently defined as 115/75 mm Hg (measured in millimeters of mercury), where the first figure represents systolic BP (SBP) and the second for diastolic BP (DBP). For patients receiving treatment for hypertension, the target of treatment is reducing blood pressure below 140/90 mm Hg. For diabetic patients, the target blood pressure is 130/80 mm Hg.

Blood pressure is controlled by a complex interaction of electrical, mechanical and hormonal forces in the body. Central sympathetic outflow directed toward the kidneys, heart, and peripheral vasculature, via efferent pathways leads to volume retention, increased cardiac output, and systemic vasoconstriction, the harbingers of persistently elevated blood pressure, i.e., hypertension. Hyper-activation of the sympathetic nervous system, especially the renal sympathetic nerves, is a major contributor to the pathophysiology of hypertension. The main electrical component of blood pressure control is the sympathetic nervous system (SNS), a part of body's autonomic nervous system which operates without conscious control.

Referring to FIG. 1, an illustration 100 depicts components of a human sympathetic nerve system 102 and the physiopathologic role of the sympathetic nerves in the regulation of blood pressure. The sympathetic nervous system 102 connects the brain 104, the heart 106, the blood vessels 108 and the kidneys 110, each of which plays an important role in the regulation of the body's blood pressure. When the blood pressure cannot be controlled within an acceptable range, another treatment option is available through the use of a catheter-based system to carry out renal denervation that reduces the sympathetic activity and eventually reduces the blood pressure.

The brain 104 plays primarily an electrical role, processing inputs and sending signals to the rest of the SNS 102. The heart 106 plays largely a mechanical role, controlling blood pressure by beating faster and harder to raise blood pressure or beating slower and less forcefully to lower blood pressure. The blood vessels 108 also play a mechanical role, influencing blood pressure by either dilating (becoming larger in diameter to lower blood pressure) or constricting (becoming smaller in diameter to raise pressure). The final, and perhaps most central actor in the regulation of blood pressure, is the kidneys 110, which play an electrical, a mechanical and a chemical role in the SNS 102. The kidneys 110 affect blood pressure by signaling (electrical) the need for increased or lowered blood pressure through the SNS 102, by controlling the amount of fluid in the body (mechanical) and by releasing key hormones (chemical) that influence the activities of the heart 106 and the blood vessels 108.

Patients with mild hypertension are advised to make behavioral and dietary changes, such as losing weight, exercising and reducing their intake of sodium and increasing their intake of potassium. If these approaches are unsuccessful, a drug treatment will usually be prescribed by the patient's physician. For a patient with resistant hypertension, denervation surgery may be introduced. Renal denervation involves disabling renal nerves within the sympathetic nervous system 102. Denervation affects both the electrical signals going from the brain 104 to the kidneys 110 as indicated by the X 112 and those emanating from the kidneys 110 as indicated by the X 114. Renal denervation has the potential to impact the mechanical and hormonal activities of the kidneys 110 and the potential to impact the electrical activation of the rest of the SNS 102. Physiology suggests that blocking sympathetic nerves leading to the kidneys 110 will reverse fluid and salt retention (lowering fluid volume and mechanical load) and reduce inappropriate renin release (stopping the deleterious hormonal renin-angiotensin aldosterone system (RAAS) cascade before it starts).

Referring to FIG. 2A, a planar view 200 depicts a kidney 202 and its corresponding renal vessel 204 and a perspective cutaway view 220 of the renal vessel 204 with a denervation catheter system 222 inserted therein. The catheter-based system 222 is delivered to the targeted renal vessel 204 through a guide catheter 224 via any conventional catheterization technique. Once the system 222 has reached a desired location, it is transformed from a rest configuration to a deployed configuration (e.g. by inflating a balloon catheter or by pulling/pushing of movable components to deploy a basket-shaped structure) to prepare for the renal denervation process. Energy (e.g. radio frequency energy or ultrasound energy) is then delivered through system electrodes to do ablation on one or more renal nerves 226. There may be multiple ablation sites during one procedure. Each ablation is performed for a predetermined time (e.g., ninety seconds) after which the deployed structure is collapsed, the catheter is pulled back a predetermined amount (e.g. one centimetre), and the catheter is rotated, the structure is deployed, and the ablation is repeated. This sequence is repeated until the denervation process is completed. Once ablation is completed at all desired sites, the system 222 is then withdrawn from the body via the same guide catheter 224. The guide catheter is then removed from the body.

There are several factors to consider in designing a catheter-based system, such as the energy type, the catheter design, and the number of electrodes. Radio-frequency energy is the most common energy type used for nerve ablation. The catheter design could be balloon-based, basket shaped or triangle shape, or any other design. Balloon-based catheter designs are preferred due to their easy deployment process, however the challenge is fabrication of electrodes on the balloon surface. The electrodes formed on the balloon surface have to be flexible and functional, withstanding the inflation and deflation of the balloon. Basket-based catheter designs, on the other hand, do not require flexible electrodes but must be able to achieve a more localized nerve ablation with electrodes being located more specifically (i.e. a more localized nerve ablation). Two main issues that could occur during nerve ablation are the restriction in blood flow during deployment of electrodes to contact the electrodes and with the vessel walls (e.g., balloon-based catheter deployment), and the flexibility of the structure during activation (also known as deployment) of the spine structure. Other issues could be sensor-related issues (such as sensitivity and range of sensors) which could hamper or prevent firm contact between the electrodes and the vessel walls for successful ablation.

A short selective guide catheter 226 is placed in each renal artery 204 under fluoroscopic guidance and heparin or bivalirudin anticoagulation. A flexible radiofrequency (RF) ablation catheter 222 is advanced to the distal renal artery 204, with typically three or more ablations performed serially, in a distal to proximal fashion in a classical helical pattern. Each ablation is positioned and performed individually through the manipulation of a deployable spine structure with different shapes. During energy delivery, the active electrode induce heat (usually <90° C. to avoid the carbonization of tissue) from the contact surface to the subjacent tissue (up to six millimeters away). The nerves 226 that reside in the adventitia of the renal artery 204 (i.e., sympathetic nerve bundles of the SNS system 102 (FIG. 1) running within the vessel adventitia) will be progressively ablated during the RF heating process. FIG. 2B illustrates a cross-sectional view 240 of a histological section of a renal artery 204 with a vessel wall 242 surrounding a vessel lumen 244 having blood 246 flowing therein and tissue surrounding the vessel wall 242 which includes the renal nerves 226.

Referring to FIG. 2C, a side planar diagram 260 depicts electrode deployment in a renal artery 204 for renal denervation using a conventional basket-shaped renal denervation system. Radio frequency (RF) ablation relies on a complete electrical circuit created through the body to conduct RF current 270. The renal denervation system includes a central mandrel 262 of the catheter 222 having a bushing 264 and spine 266 structure coupled around the mandrel 262 for thrusting an RF electrode 268 against the vessel wall 242 when the spine 266 is fully deployed. The RF current 270 is able to pass through tissue because of the abundance of ionic fluid present; however, tissue is not a perfect conductor and the RF current 270 causes resistive heating (the Joule effect) within the tissue. Thus, direct RF heating occurs within several millimeters of the applicator (the active RF electrode 268). The rest of the final ablation zone is created in more peripheral areas around the electrode 268 due to thermal convections.

The RF current 270 can be applied using monopolar or bipolar modes. In monopolar mode, a single interstitial electrode (or group of electrodes) 268 is used to deliver current 270 at the targeted ablation region, while ground (GND) electrodes 272 (usually very large and placed outside the body) complete the electrical path through the body. In bipolar mode, current flows between two interstitial electrodes. Bipolar mode generally has the advantages of (a) focused and more effective heating in the area between the electrodes, (b) reduced dependence on background conductivity, and (c) no need for ground pads. However, bipolar mode requires additional electrode pairs (requiring extra space within the lumen) and does not heat well in the radial direction away from contact surface into the surrounding tissue.

On the other hand, monopolar mode has the advantages of (a) a wider zone of heating around each electrode 262, and (b) limited invasiveness due to a simple footprint of the electrode 262, thereby providing wider clinical versatility.

Conventional renal denervation systems include balloon designs and basket-shaped designs. Basket-shapes designs include discrete spine structures packaged together with a bushing structure into the catheter or shaft body. The electrodes and/or sensors and electrical wire interconnections are assembled on the spines. After being deployed, the electrodes form a triangular shape and, unlike the balloon designs, do not restrict blood flow during the denervation procedure.

Despite clinical impact and successful demonstration of denervation using conventional renal denervation systems on humans, the integration of each mechanical component (e.g. RF electrode, spine) of the conventional renal denervation systems has remained a complicated process with less standardized procedures and almost complete manual assembly. For example, some conventional basket-shaped spine structures require the electrodes to be glued on each separate spine after welding the RF traces onto each oval electrode. The sequential spine assembly process is also carried manually and both each spine connection and other electrical connections need to be carefully aligned into the bushing before being packaged on the catheter. In addition to the electrodes, the sensors packaged on the spines include RF electrodes and temperature sensors. The electrical wire interconnections must also include many sensor input/output (I/O) connections which contribute to the amount of assembly work required for the conventional basket-shaped denervation systems. And, as discussed above, all of the assembly work is typically manual and time consuming.

In addition to the fabrication difficulties, conventional renal denervation systems require external imaging systems for accurate ablation locating. Choosing optimal reno-vascular imaging modalities presents another clinical concern. The primary goal of using such visualization steps is to assure a good contact of the RF electrodes 268 against the vessel wall 242 to provide a more effective ablation. Due to insufficient resolution with a duplex ultrasound imaging devices, conventional computed tomography (CT) angiography is typically used to provide high resolution surveillance during the denervation process. However, CT angiography poses a high radiation risk and is considered unnecessary in patients who are clinically stable. Alternatively, non-contrast enhanced magnetic resonance (MR) angiography with electrocardiogram (ECG) and respiratory gating uses fast steady-state gradient echo imaging to obtain high-resolution angiographic images. Yet, these angiography methods do not provide continuous monitoring during the electrode deployment process inside the vessel. This real time monitoring is crucial for all surgeons, and particularly crucial for a surgeon with less practical experiences.

In accordance with a present embodiment, an apparatus for improved renal nerve ablation is proposed which provides integrated effective contact monitoring without requiring external monitoring systems such as MR imaging or CT imaging and efficient scalable assembly processes which reduce the amount of assembly work required as well as improve the contact between the electrodes/sensors and the vessel tissue for effective renal nerve ablation.

Figures 3A, 3B:
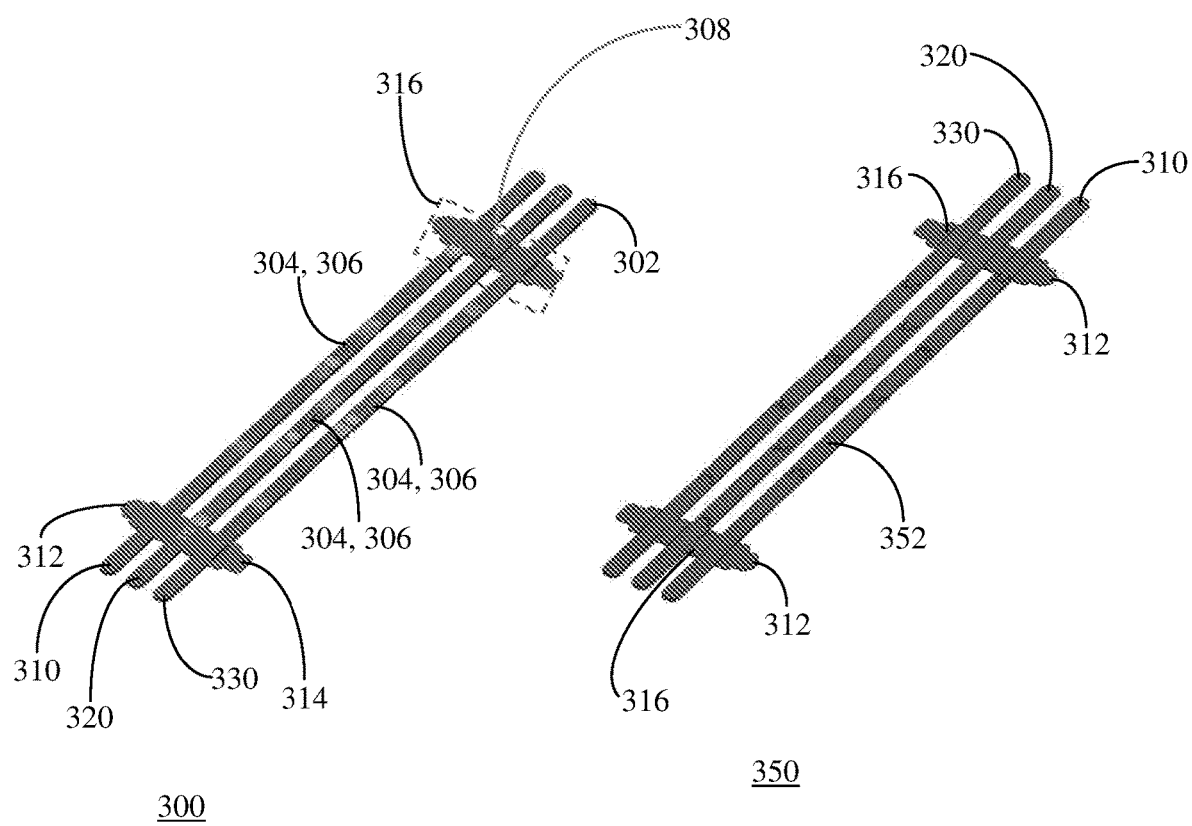

Referring to FIGS. 3A and 3B, perspective views 300, 350 depict a fabricated spine structure for a renal denervation system in accordance with a present embodiment. The front top right perspective view 300 depicts the top of the spine structure in accordance with the present embodiment and the front bottom left perspective view 350 depicts the bottom of the spine structure in accordance with the present embodiment. The proposed roll-up structure in accordance with the present embodiment includes a one-piece polymeric substrate 302 with a rigid stiffener 352 having integrated sensors 304 and electrodes 306 such as tactile sensors, temperature sensors and RF electrodes. Parylene C (by Specialty Coating Systems, SCS) is chosen as the polymeric substrate 302 material due to its biocompatibility and biostability as well as its flexibility. However, a Parylene substrate has too much flexibility which can be an issue during ablation as it may not be able to maintain the desired shape during ablation process. Therefore, the addition of the rigid stiffener 352 (e.g., a Si stiffener) to the backsides of the structure help the spine structure to maintains its shape. In accordance with the present embodiment, the rigid stiffener will only be incorporated at specific locations to maintain the flexibility of the spine structure ensure that it can still be bent at predetermined locations.

As seen in the views 300, 350, there are three spines 310, 320, 330 in each structure and the sensors 304 are integrated onto the spines 310, 320, 330 at different locations. The advantage of having the one-piece structure and integrated sensors 304 on the spines 310, 320, 330 is a significant reduction in the amount of assembly and packaging work. There is also an integrated multiplexer 308 to provide a multiplexed design included to reduce the number of wire connections, further facilitating the assembly and packaging work and device miniaturization. The one-piece, three-spine structure eliminates the need to assemble individual spines together and does not require additional components to package the assembled spines into the catheter as the one-piece structure can be rolled-up and secured by inserting tabs 312 into slots 314. Epoxy or encapsulants can be applied to the tab-slot cross-spine structures 316 to further secure the tab-slot structures 316 on the substrate.

Figure 4:
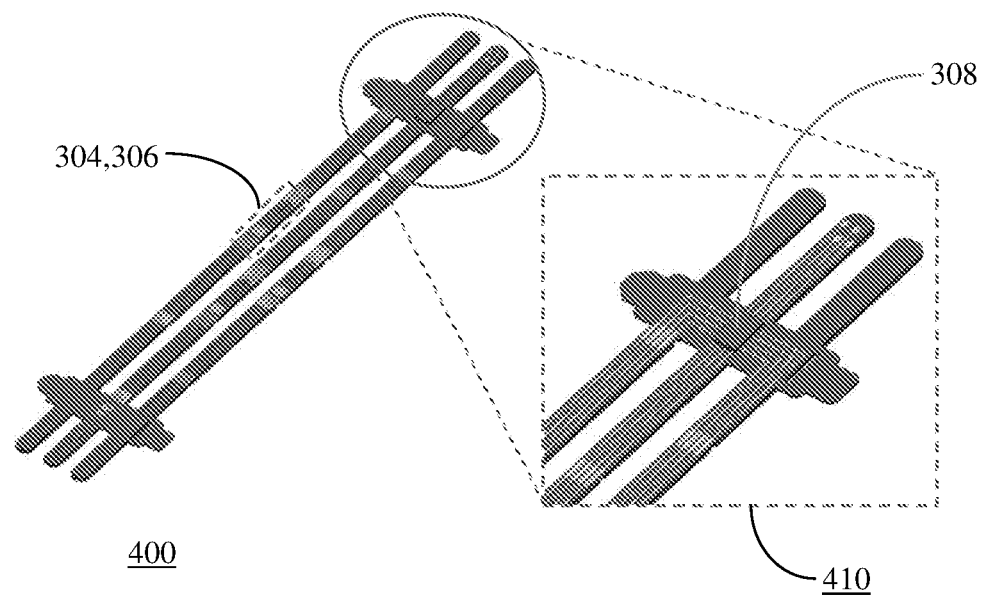
FIG. 4 depicts a front top right perspective view of the spine structure highlighting integrated sensors and electrodes in accordance with the present embodiment wherein an inset further highlights the multiplexer design of the spine structure in accordance with the present embodiment to minimize the numbers of signal wires.

Referring to FIG. 4, a front top right perspective view 400 of the spine structure highlights the integrated sensors 304 and electrodes 306 wired in a multiplexed design in accordance with the present embodiment to minimize the numbers of signal wires. An inset 410 further highlights the multiplexer design of the spine structure showing the reduced wiring interconnections from the multiplexer 308 through the catheter to the operator circuitry.

Figure 5A:
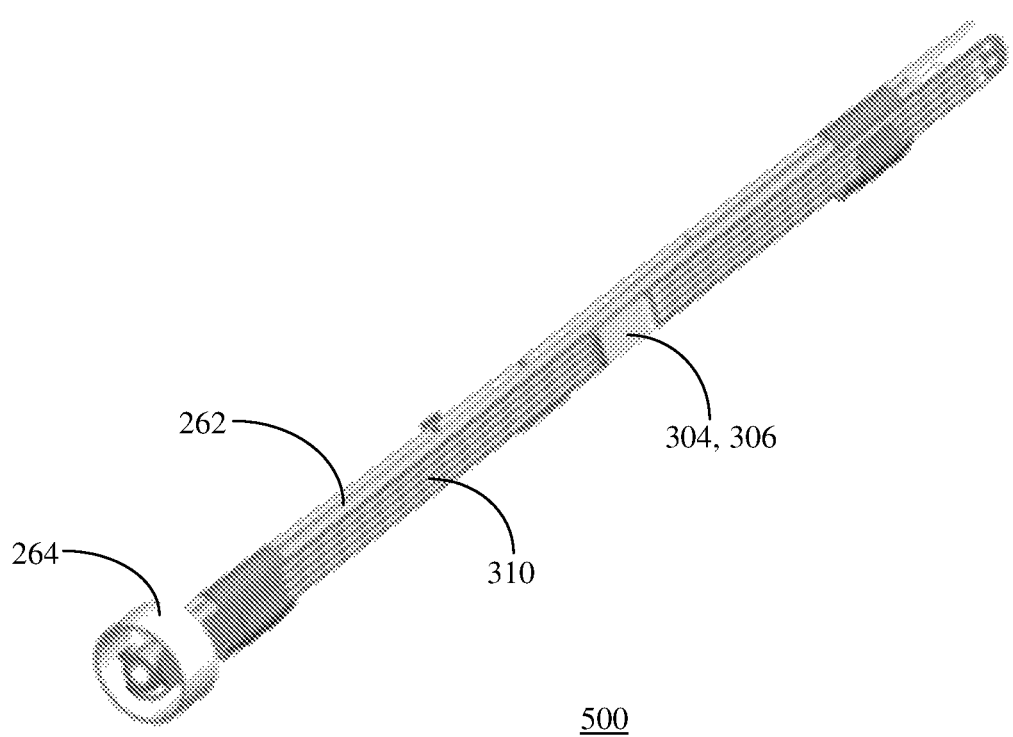
Figure 5B:
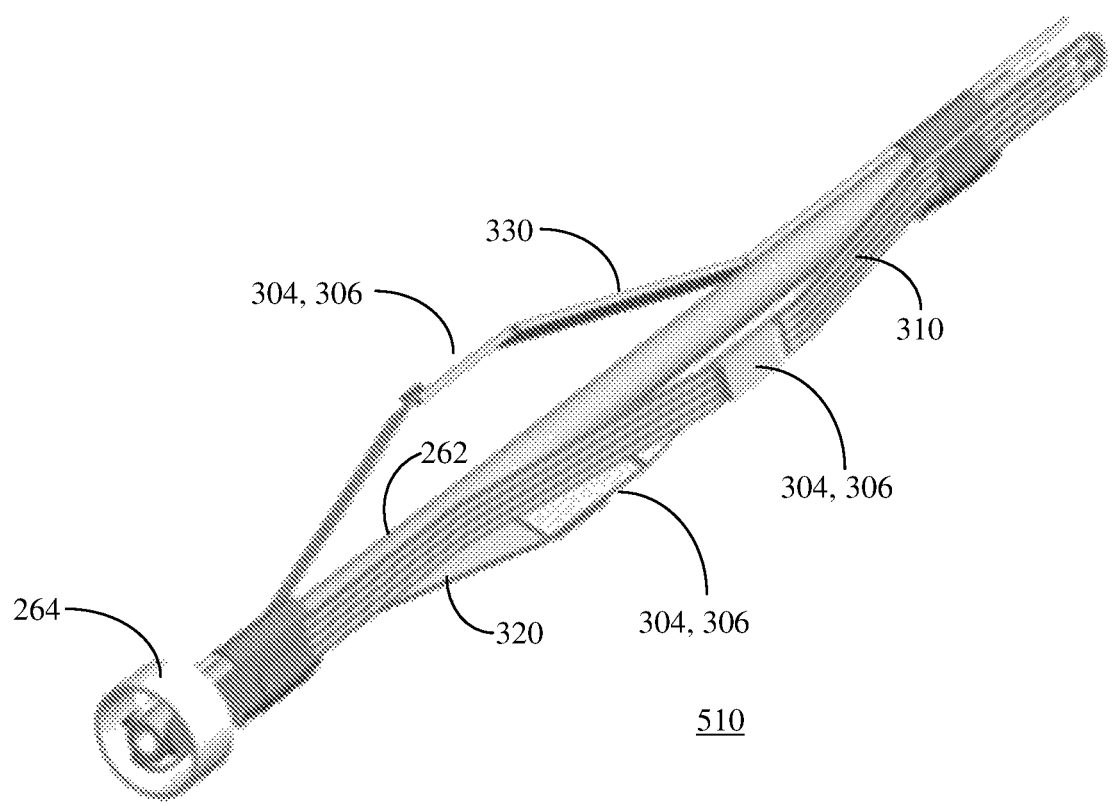
Figure 5C:
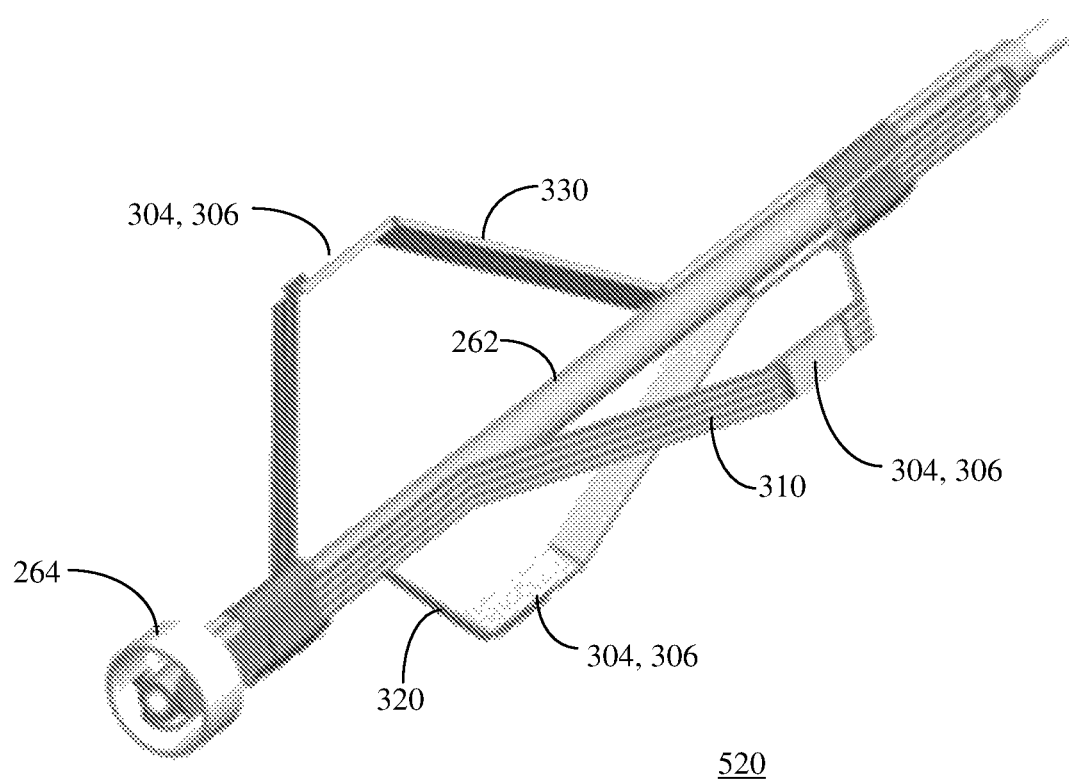

Referring to FIG. 5, front top right perspective views 500, 510, 520 illustrating operational deployment of the spine structure depicted in the views 300, 350, 400 wrapped around a catheter mandrel 262 in accordance with the present embodiment. The bushing 264 secures the rolled-up three-spine structure to the catheter mandrel 262. The rolled-up spine structure can be packaged with the guide wire tube and activation tube. Upon reaching the targeted region in the renal vessel, the system will transform from a rest configuration to a deployed configuration to enable contact of the integrated sensors 304 and the electrodes 306 to the vessel walls. The perspective view 500 depicts the undeployed spine structure at rest. The perspective view 510 depicts the spine structure semi-deployed between the at rest configuration and the fully deployed configuration. The perspective view 520 depicts the spine structure fully deployed around the catheter. The diameter of the spine structure in the full deployment configuration can be greater than nine mm.

Figure 6B:
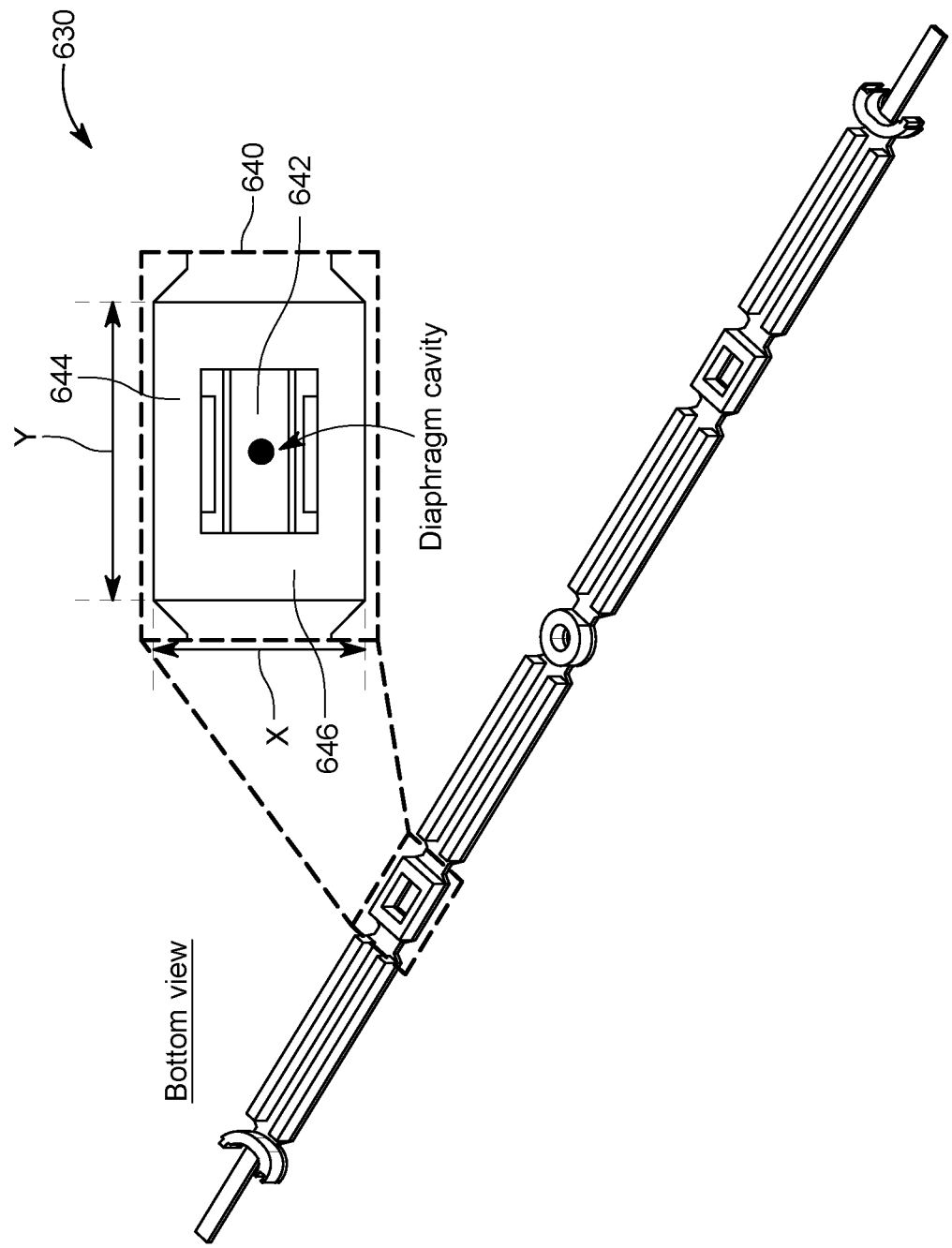

In addition to the spine design of the novel and robust structure in accordance with the present embodiment, a tactile function is integrated onto the structure in accordance with two designs. Referring to FIGS. 6A and 6B, perspective views 600, 630 depict the fabricated spine structure in accordance with the present embodiment incorporating the tactile function in accordance with a first design. The perspective view 600 depicts a front top left perspective view of a two-spine structure highlighting an upper portion of a tactile sensor structure in an inset 610. The perspective view 630 depicts a front bottom right perspective view of the two-spine structure highlighting a bottom portion of the tactile sensor structure in an inset 640. In accordance with the first design, a pressure cavity 642 is created from the backside of the silicon substrate to achieve a diaphragm-based force sensor. Meander-shaped metallic gauges 612 are patterned on a frontside of the polymerized structure along edges 644, 646 of the pressure cavity 642 for the detection of external pressure/force. The metallic gauges 612 are formed on either side of the RF electrode 306 and when the RF electrode 306 touches the vessel wall 242, diaphragm deflection will be induced and detectable by the metallic gauges 612. The metallic gauges 612 will detect an exact moment of contact and will continue monitoring a force of the vessel wall contact through output changes of the metallic gauges 612. In this way, the metallic gauges 612 serve as impedance change elements and enable monitoring of the force of the vessel wall contact by changing impedance in response to mechanical bending of the metallic gauges 612.

Figure 6C:
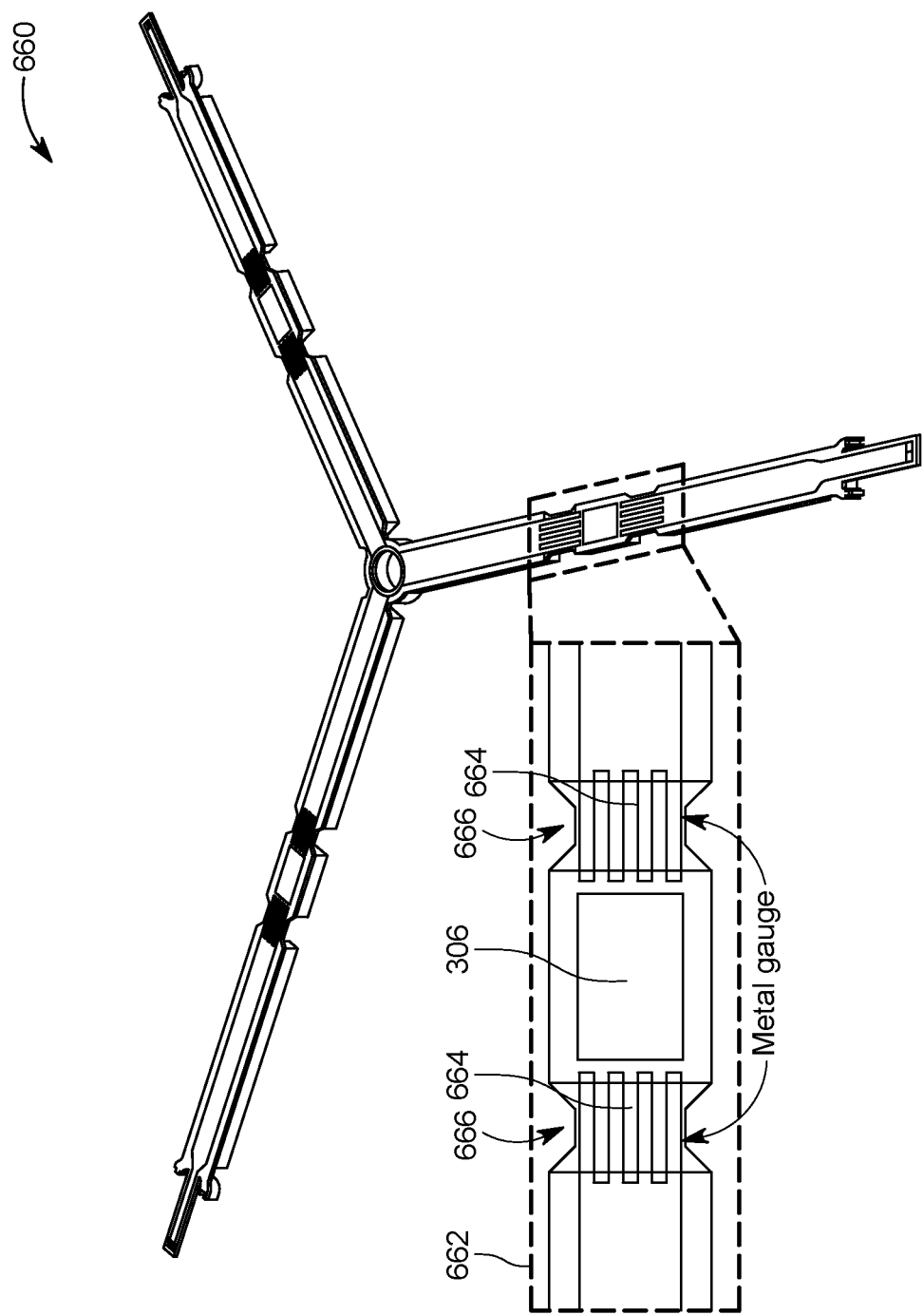

Referring to FIG. 6C, a front top left perspective view 660 of a three-spine structure includes an inset 662 depicting a tactile sensor structure in accordance with a second design.

In accordance with the second design, metallic gauges 664 are patterned along soft joint regions 666 where the maximum mechanical bending moment occurs during full deployment. In response to lateral movement being generated by external forces, the output of the metallic gauges 664 increases until the central ablation electrode 306 contacts the vessel wall 242 and stops expansion in the structure's radial direction (i.e., when the electrode 306 is in firm contact with the vessel wall 242). Any loss of contact between the electrode 306 and the vessel wall 242 will be transferred into output variations from the metallic gauges 664.

Figure 7A:
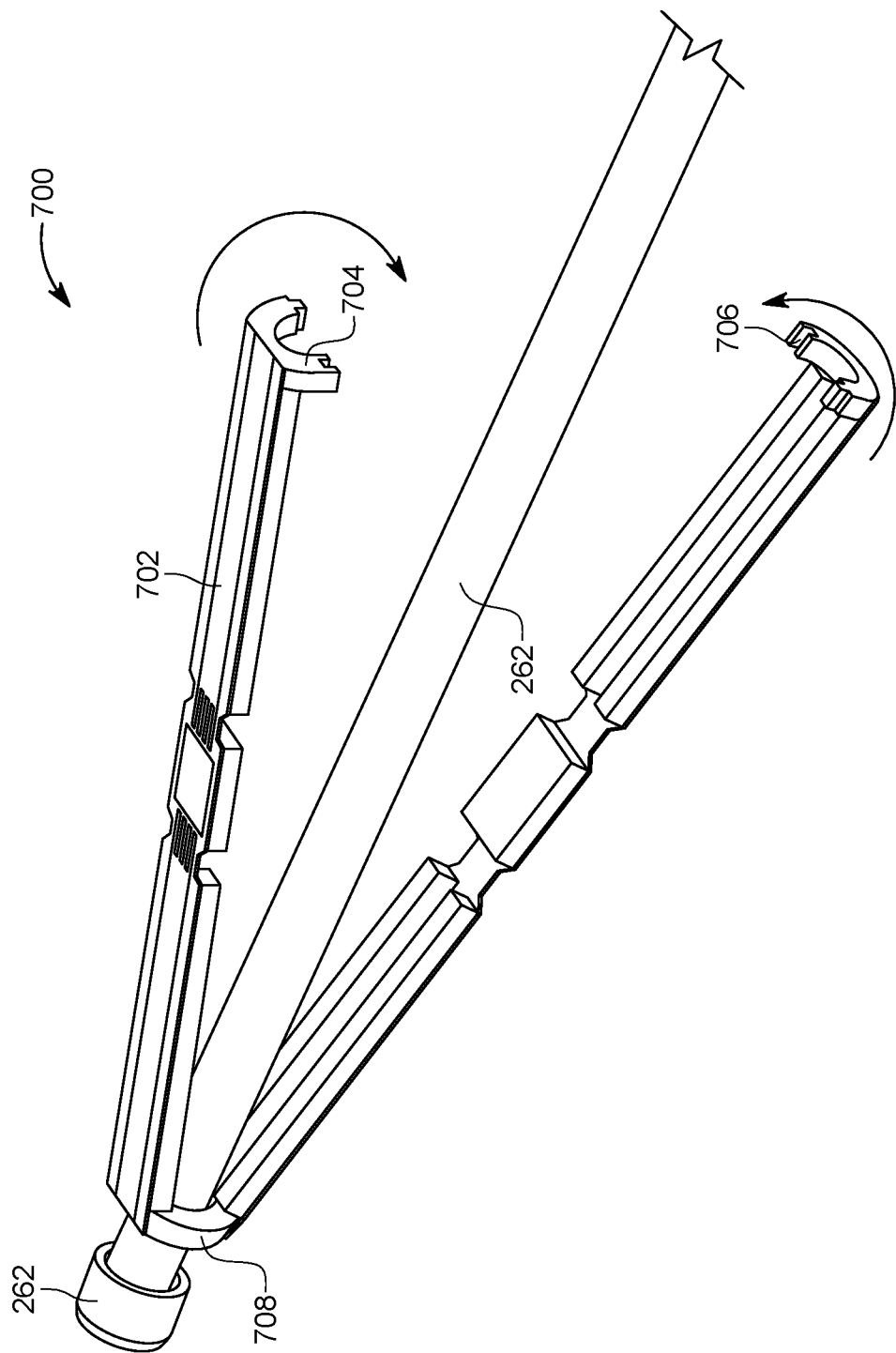
Figure 7B:
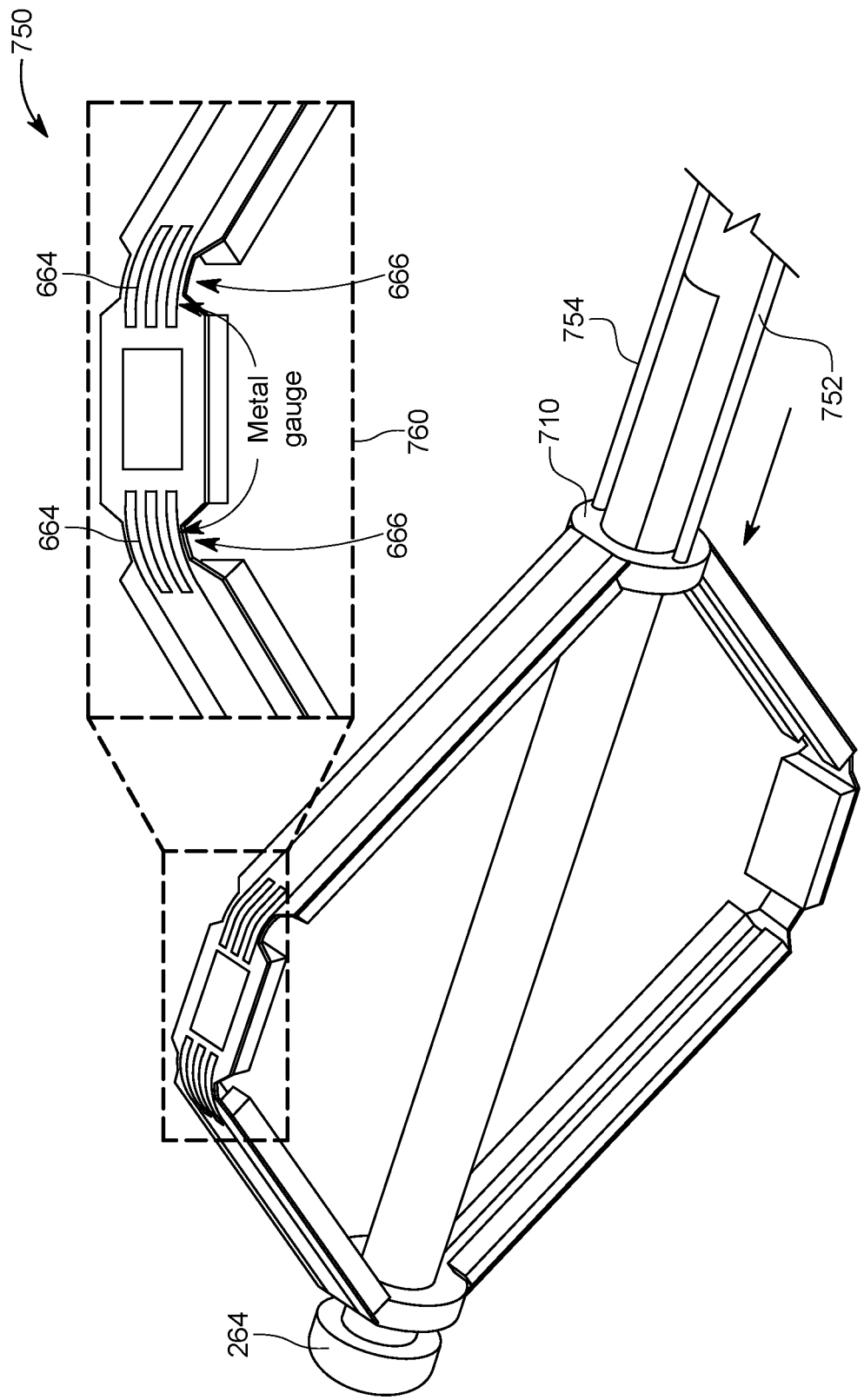
Figure 9A:
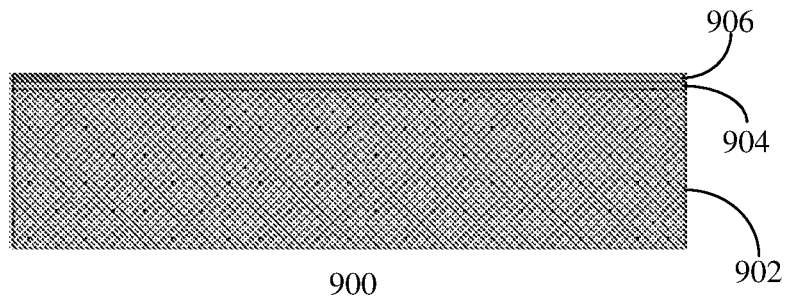
FIGS. 9A, 9B, 9C and 9D, depicts side planar cutaway views of fabrication steps of the spine structure with integrated sensor and electrode devices in accordance with an alternate embodiment.
Figure 9B:
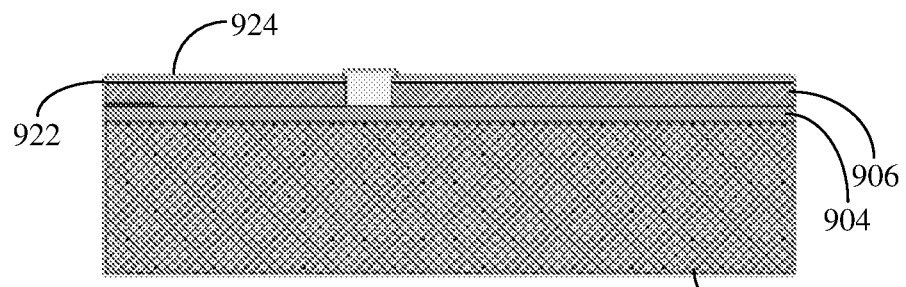
Figure 9C:
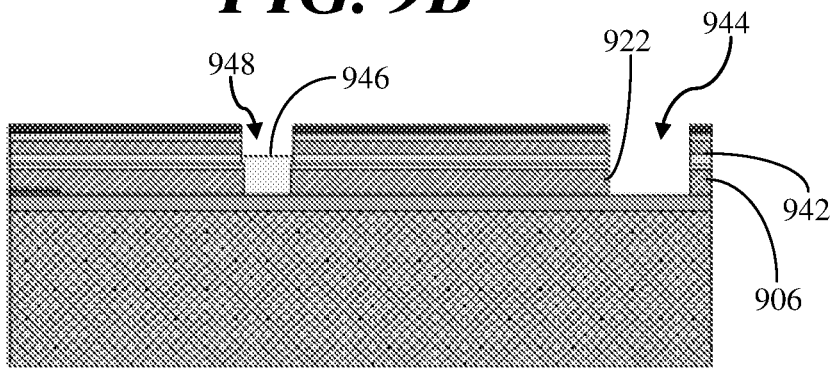
Figure 9D:
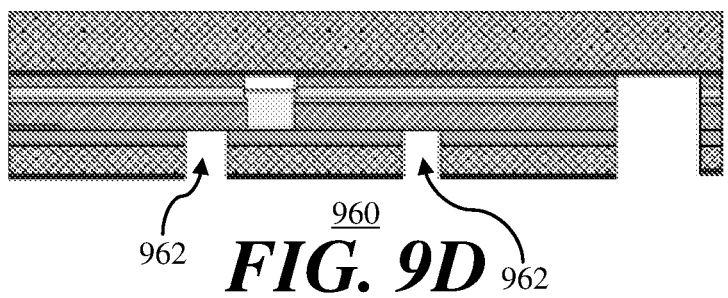

The assembly of the deployable multi-spine structure onto the mandrel (or catheter) 262 is demonstrated in FIG. 7. FIG. 7A depicts a front top right perspective view 700 of the two-spine structure 702 as it is assembled around the mandrel 262. The total thickness of the silicon stiffener 352 (FIG. 3B) can be up to 400 μm which is strong enough to stand mechanical impacts during a clamping as shown in the view 700. Adhesive is applied between two clamped half rings 704, 706 to form with the tab and slot 312, 314 connection at a first end of the multi-spine structure a first linkage to assemble the structure 702 around the mandrel 262. A first clamped structure 708 adjacent to the bushing 264 and the tab and slot 312, 314 connection at a second end of the multi-spine structure forms a second linkage to assemble the structure 702 around the mandrel 262. Referring to FIG. 7B, a front top right perspective view 750 depicts the two-spine structure 702 around the mandrel 262 in a fully deployed configuration. A second clamped structure 710 consisting of the two clamped half rings 704, 706 adhesived together is formed around the mandrel 262 and pushing wires 752, 754 are glued to the second clamped structure 710 for the manipulation of lateral mechanical movement. An inset 760 depicts a magnified view of the vessel wall contact portion of the spine showing the second design of the tactile force sensing principle (i.e., the metallic gauges 664 patterned along the soft joint regions 666).

Referring to FIGS. 8A, 8B, 8C and 8D, side planar cutaway views 800, 820, 840, 860 of fabrication steps for batch fabrication of the spine structure with integrated sensor and electrode devices in accordance with the present embodiment are depicted. The fabrication starts with a bare silicon substrate 802 fabricateable at wafer level for high throughput and improved scalability. The silicon substrate 802 serves as the mechanical stiffener for the spine structure in accordance with the present embodiment. Anchors 804 (small trenches) are defined in the silicon surface as shown in the side planar view 800. The anchors 804 facilitate good adhesion between the silicon substrate and a cladding polymer layer 822 conformably coated on the silicon substrate 802 as shown in the side planar view 820. A metal layer 842 of a conductive metal such as gold (Au) or platinum (Pt) is then deposited and patterned to form metallic gauges and active electrodes on the polymer layer 822 as shown in the side planar view 840. Lastly, spine releasing and backside pressure cavities 862 are etched through a silicon etching process such as a deep reactive ion etch (DRIE) process as shown in the side planar view 860.

Referring to FIGS. 9A, 9B, 9C and 9D, side planar cutaway views 900, 920, 940, 960 of fabrication steps of the spine structure with integrated sensor and electrode devices in accordance with an alternate embodiment are depicted. The fabrication process starts with deposition of a nitride layer 904 on a silicon substrate 902 on an eight-inch silicon wafer followed by coating of a 10 um Parylene C layer 906 as shown in the side planar view 900. An oxide layer 922 is deposited on the Parylene C layer 906 to improve adhesion of metal traces on the spine structure (i.e., on the oxide layer 922) as shown in the side planar view 920. Next the conductive metal traces 924 (e.g., titanium (Ti) or Au) are patterned on the wafer by a lift-off method.

A top 10 um Parylene C layer 942 is deposited to cover the metal traces 924. Then the roll-up spine structure is defined by etching 944 both the Parylene C layers 906, 942 and the oxide layer 922 and the bonding pads 946 are opened as well by etching 948 the Parylene C layer 942 to expose the metallic bonding pads 946 as shown in the side planar view 940. In order to form the silicon stiffeners at specified locations, a deep reactive ion etch (DRIE) and nitride etch 962 is carried out at the backside of the wafer as shown in the side planar view 960. The wafer is then heated to about 180° C. to release the spine structure from the thermal tape.

After the roll-up spine structure is released from the structure, the integrated sensors can be assembled onto the structure with epoxy which is non-electrically and non-thermally conductive. Connection between the sensors and the spine structure can be created by wire bonding. As mentioned above, the multi-spine structure can be rolled-up and secured by inserting the tab 312 into the slot 314 (FIG. 3A) which can be further secured with epoxy or encapsulants. A customized jig can be fabricated to assist in rolling up the spine structure.

It is obvious that both the RF electrodes 306 and the number of spines 310, 312, 314 can be defined in accordance with the present embodiment by standardized batch processes instead of tedious post assembly manual processes. Although only two- and three-spine designs are disclosed herein, those skilled in the art will realize that using either of the process flows (FIGS. 8 and 9) and existing MEMS technology, the total number of spines and, thereby, the total number of ablation sites can be increased as needed.

Figure 10A:
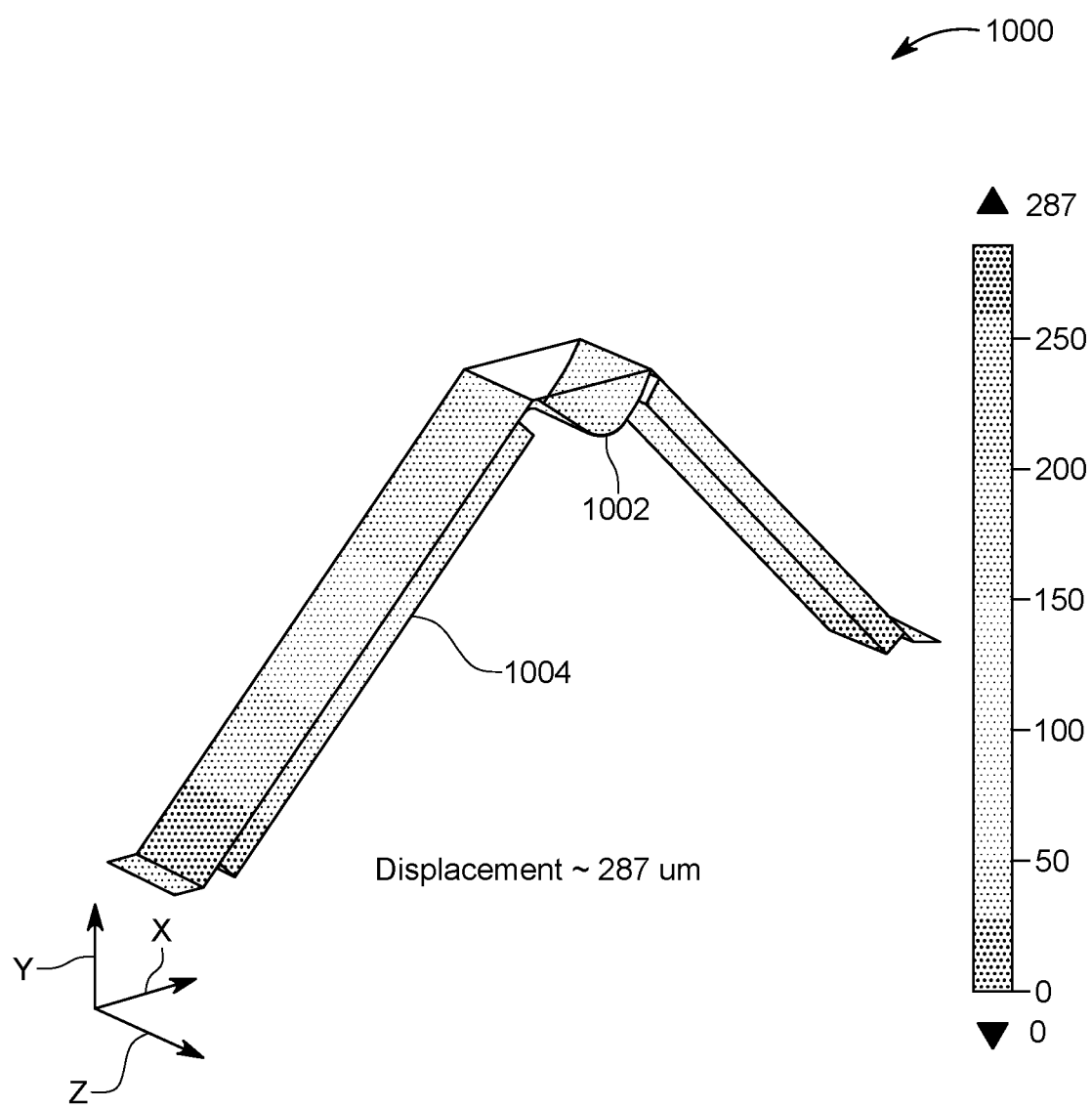
Figure 10B:
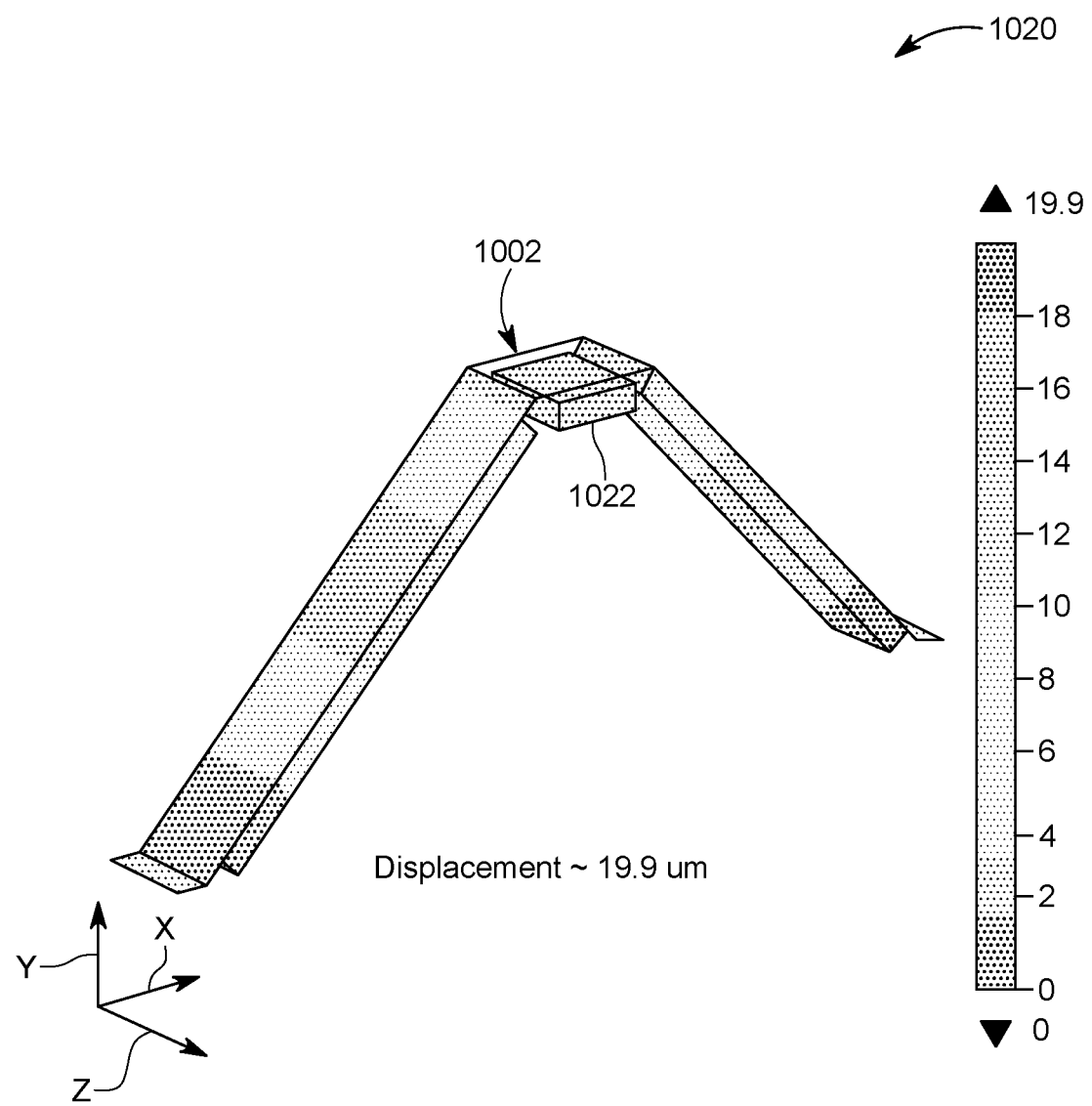
Figure 10C:
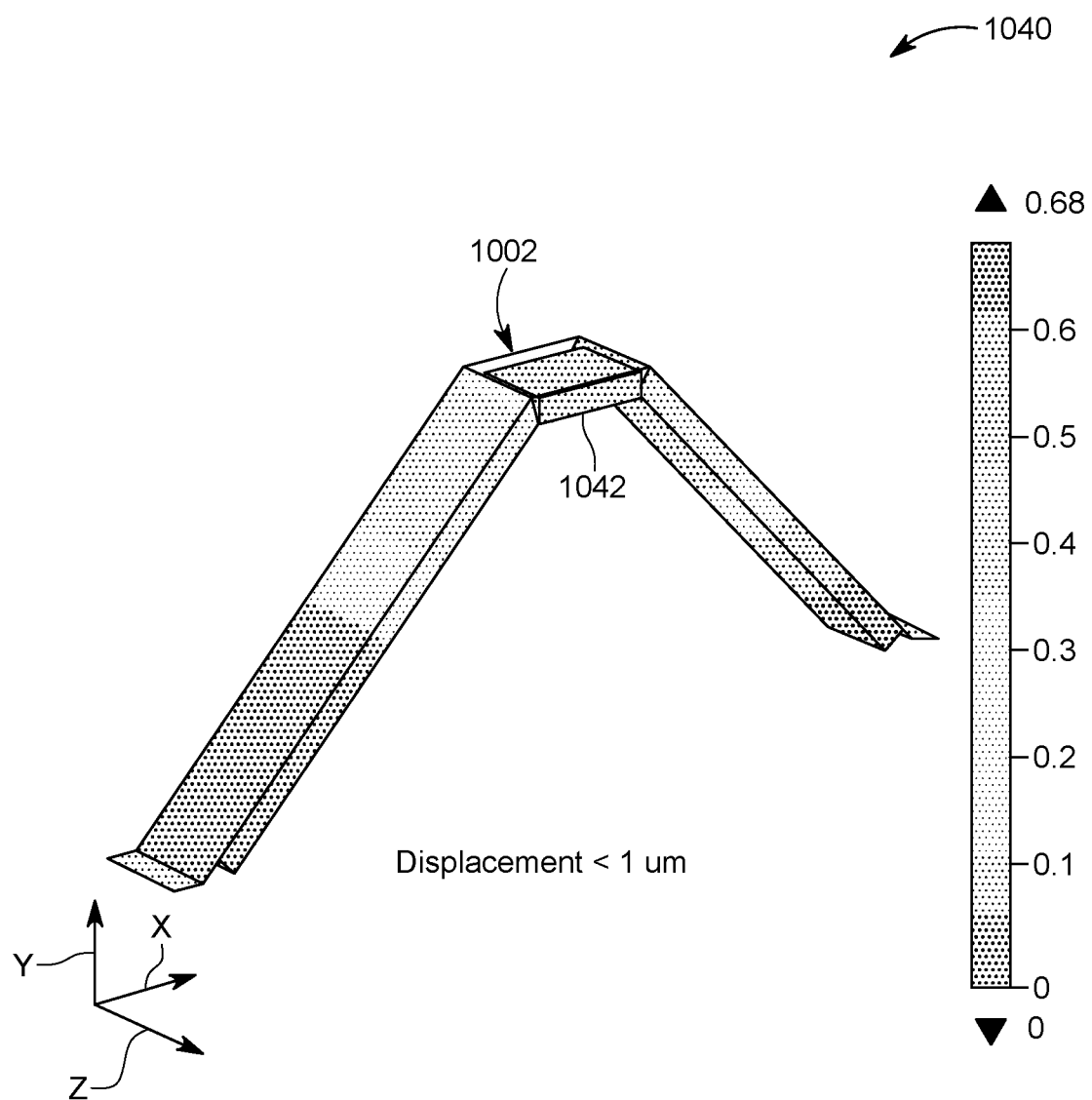

In accordance with the present embodiment, the silicon substrate 352 will effectively reinforce mechanical stability of the spine structure. FIGS. 10A, 10B and 10C, depict illustrations 1000, 1020, 1040 of simulation-measured displacement forces on the spine structure in accordance with the present embodiment with different thicknesses of the silicon stiffener 352. Referring to the illustration 1000, a simulation of mechanical displacement due to under contact on a central block 1002 of a spine structure 1004 with no silicon stiffener behind the spine structure's denervation electrode is depicted. With a fixed substrate thickness of 350 µm, the illustration 1000 shows that the central block 1002 with only polymer material will not sustain an external loading (estimated contact force ~50 mN) at the moment of contact with the vessel wall 242.

The illustration 1020 (FIG. 10B) depicts simulation-measured displacement forces on the spine structure with a one millimeter (mm) thick silicon stiffener behind the spine structure's denervation electrode. After adding the one mm silicon block 1022, the deflection is drastically reduced due to the improvement of mechanical stiffness. However, the area covered by the silicon stiffener also has to be optimized for an acceptable displacement on the central block 1002.

The illustration 1040 (FIG. 10C) depicts simulation-measured displacement forces on the spine structure with a 1.4 mm thick silicon stiffener behind the spine structure's denervation electrode. In accordance with the present embodiment, optimal deformation is provided when the total dimensions of the top polymer layer of the central block 1002 is 1.5×1 mm$^2$ with a silicon stiffener 1042 dimension of 1.4×1 mm$^2$, dimensions which introduce not only enough strain on the metallic gauges 664 (FIG. 6C), but also a reasonable displacement before any mechanical fracture of the spine structure.

Figure 11A:
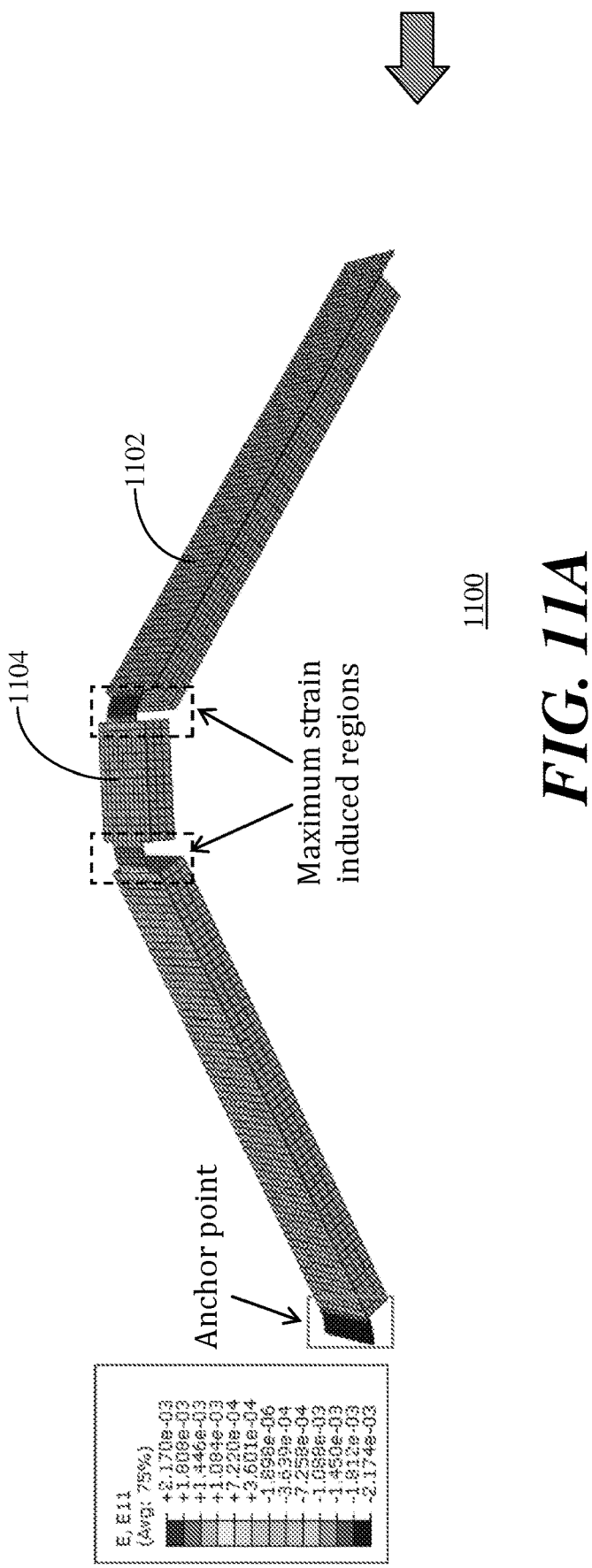
Figure 11B:
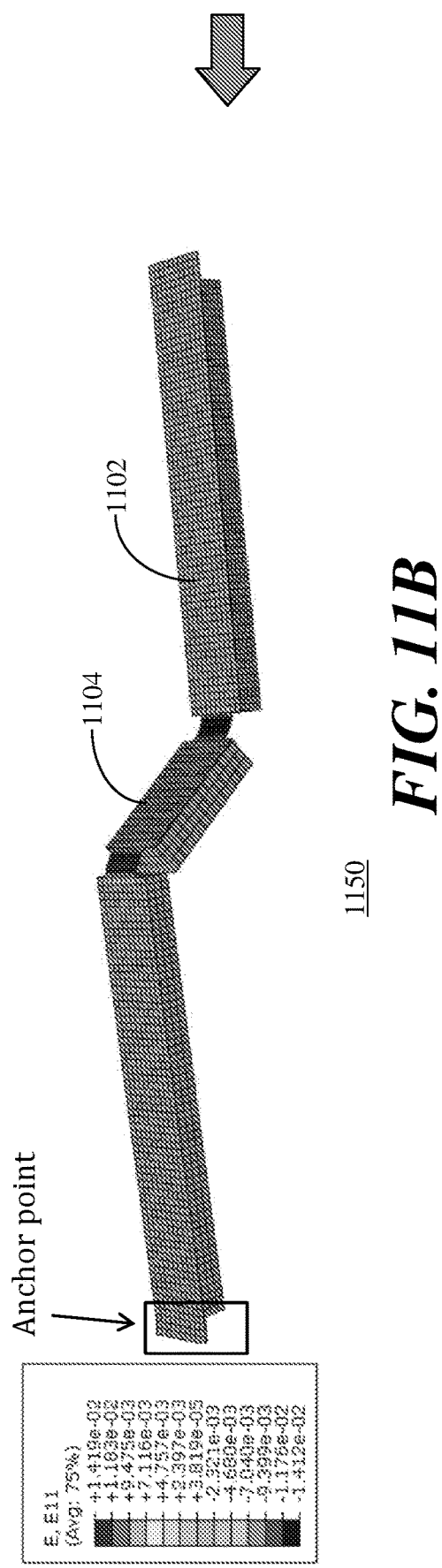

FIGS. 11A and 11B depict strain diagrams 1100, 1150 of bending modes of the spine structure in accordance with the present embodiment. Besides optimization of the central stiffener size, additional simulations were conducted to predict the tactile function, wherein the strain diagram 1100 depicts a fully deployed spine structure in a first bending mode and the strain diagram 1150 depicts a strain diagram of a partially deployed spine structure in a second bending mode. The strain diagrams 1100, 1120 elucidate the bending modes of the spine structure 1102 before its mechanical failure moment, when the central block 1104 starts tilting instead of expanding in a radial direction. As aforementioned, the maximum strain is induced at the soft joint region and the average strain generated is up to 1.4%. Assuming the total resistance of metallic gauges 664 is a few hundreds Ohms, the reasonable output change is in a range of a few Ohms. Such ohmic change can be clearly differentiated, even with a conventional multimeter.

Thus, it can be seen that the present embodiment can provide a roll-up spine structure with integrated sensors which can be packaged with a catheter to be inserted into renal vessels of patients with resistant hypertension for renal denervation. The spine structure is able to achieve effective contact between the electrodes 268 and the vessel walls 242 (FIG. 2C) for the renal denervation process. The one-piece design of the structure together with integrated sensors reduces assembly and packaging effort required.

The present embodiment also provides integrated tactile sensors 304 in a renal denervation catheter system providing improved detection of firm contact between the electrodes 268, 306 and the vessel walls 242 and enhanced nerve ablation accuracy. The roll-up spine structure in accordance with the present embodiment can be easily manufactured with scalable fabrication techniques whereby monolithically micro-machined multiple sensors and electrodes can be integrated during manufacture with the structure. The electrodes include a RF electrode or heater for the nerve ablation. The multiple sensors include temperature sensors and tactile sensors. As the sensors are not being assembled onto the spines of the roll-up structure individually and, instead, integrated into the fabrication of the roll-up structure to obtain the one-piece structure, less manual effort is needed to fabricate and assemble the renal denervation catheter in accordance with the present embodiment. In addition, tactile sensing capability of the renal denervation catheter in accordance with the present embodiment ensures effective contact between the renal vessel wall 242 and the electrodes 268. The rigid-flexible substrate in accordance with the present embodiment is obtained by integrating a polymer material with a stiffening material (e.g., silicon) during manufacture to ensure flexibility of the device while maintaining stiffness upon activation of the spine structure for nerve ablation. While any polymer material can be used for the multi-spine structure, Parylene C provides optimal benefits due to its biocompatibility and high flexibility. Also, deep reactive ion etching on the backside of the silicon wafer is carried out to form the rigid stiffener at specific location to achieve and maintain stiffness upon activation of spine structure for nerve ablation.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A method of batch fabricating a plurality of catheter arms for vascular denervation comprising:
   depositing a first polymer coating on a semiconductor substrate;
   forming metal traces on the first polymer coating;
   patterning and etching the substrate to the first polymer coating to create flexible joint regions; and
   fabricating the plurality of catheter arms with flexible joint regions.

2. The method in accordance with claim 1 wherein depositing the first polymer coating on the semiconductor substrate comprises:
   anchor trenching the substrate; and
   depositing the first polymer coating on the semiconductor substrate including depositing the first polymer coating into the anchor trenches for enhanced adhesion between the first polymer coating and the semiconductor substrate.

3. The method in accordance with claim 1 wherein depositing the first polymer coating on the semiconductor substrate comprises:
   depositing a nitride layer on the semiconductor substrate; and
   depositing the first polymer coating on the nitride layer.

4. The method in accordance with claim 1 wherein forming the metal traces on the first polymer coating comprises:
   depositing an oxide layer on the first polymer coating for enhanced adhesion of the metal traces;
   forming the metal traces on the oxide layer; and
   depositing a second polymer coating to cover the metal traces.

5. The method in accordance with claim 4 wherein depositing the second polymer coating comprises patterning and etching the second polymer coating to expose the metal traces.

6. The method in accordance with claim 1 wherein patterning and etching the substrate to create the flexible joint regions comprises deep-reactive-ion-etching the semiconductor substrate from a backside of the semiconductor substrate such that the flexible joint regions do not comprise any of the semiconductor substrate.

7. The method in accordance with claim 1 wherein the polymer coating is a patternable polymer material.

8. The method in accordance with claim 1 wherein the semiconductor substrate is silicon.

9. The method in accordance with claim 1 wherein the metal traces include one of more of titanium, gold, nickel, copper, chromium, aluminium, indium, platinum, sliver silver and tin.

10. The method in accordance with claim 1 wherein forming the metal traces comprises forming circuitry on the first polymer coating.

11. The method in accordance with claim 10 wherein the circuitry comprises one or more metallic gauges for tactile sensing.

12. The method in accordance with claim 10 wherein the circuitry comprises one or more electrodes for nerve ablation.

13. The method in accordance with claim 10 wherein the circuitry comprises one or more temperature sensor for a temperature measurement of nerve ablation.

14. A device for vascular denervation comprising:
   a catheter for insertion into a vessel;
   a plurality of catheter arms disposed around the catheter, wherein the plurality of catheter arms is batch fabricated using a method as claimed in claim 1,
   the plurality of catheter arms comprises alternating regions of flexible joints and rigid blocks along the plurality of catheter arms, wherein each of the plurality of catheter arms comprises:
   two or more sensors disposed on each of the plurality of catheter arms, the two or more sensors comprising at least one tactile sensor and at least one temperature sensor;
   at least one electrode disposed on each of the plurality of catheter arms for nerve ablation; and
   electrical circuitry disposed on each of the plurality of catheter arms and coupled to inputs and outputs of the at least one electrode and the at least one sensor; and
   at least one linkage connected to the plurality of catheter arms at substantially an end of the plurality of catheter arms for wrapping the plurality of catheter arms around the catheter.

15. The device in accordance with claim 14, wherein the linkage is formed to have a ring structure and the plurality of catheter arms is formed radially around the ring structure of the linkage at a first end thereof such that the device is assembled by inserting the catheter through the ring structure and wrapping the plurality of catheter arms around the catheter and securing the plurality of catheter arms to each other at a second end distal to the first end.

16. The device in accordance with claim 14, wherein the linkage is formed to have a tab-slot structure at either end thereof and the plurality of catheter arms is formed parallel to one another such that the device is assembled to wrap around the catheter and be secured by inserting the tab into the slot.

17. A method for vascular denervation comprising:
   inserting a device including a catheter into a vessel;
   deploying at least one catheter arm of a plurality of catheter arms of the device until it makes contact against a wall of the vessel, the plurality of catheter arms disposed around the catheter, wherein the plurality of catheter arms is batch fabricated using a method as claimed in claim 1;
   monitoring an amount of contact of the at least one catheter arm with the wall of the vessel to determine that the amount of contact does not restrict fluid flow in the vessel and the amount of contact is sufficient for the vascular denervation by using at least one tactile sensor disposed on one of the at least one catheter arm; and
   ablating targeted nerves by energizing at least one electrode disposed on one of the at least one catheter arm when in contact with the blood wall of the vessel,
   wherein the tactile sensor determines that the amount of contact is sufficient for the vascular denervation in response to impedance detected by an impedance change element of the tactile sensor.

* * * * *